United States Patent [19]
Yang et al.

[11] Patent Number: 5,580,759
[45] Date of Patent: Dec. 3, 1996

[54] CONSTRUCTION OF RECOMBINANT DNA BY EXONUCLEASE RECESSION

[75] Inventors: Yih-Sheng Yang, Garland; Philip W. Tucker; J. Donald Capra, both of Dallas, all of Tex.

[73] Assignee: Board of Regents, The University of Texas System, Austin, Tex.

[21] Appl. No.: 192,300

[22] Filed: Feb. 3, 1994

[51] Int. Cl.$^6$ .......................... C07H 21/04; C12P 19/34; C12Q 1/68

[52] U.S. Cl. .......................... 435/91.1; 435/6; 435/91.2; 435/91.4; 435/91.5; 435/91.53; 935/77; 935/78

[58] Field of Search .............................. 435/6, 91.1, 91.2, 435/91.4, 91.5, 91.53; 935/77, 78

[56] References Cited

U.S. PATENT DOCUMENTS

| | | | |
|---|---|---|---|
| 5,162,209 | 11/1992 | Scheele | 435/91 |
| 5,391,480 | 2/1995 | Davis et al. | 435/6 |
| 5,407,813 | 4/1995 | Gold | 435/91.1 |

FOREIGN PATENT DOCUMENTS

| | | | |
|---|---|---|---|
| 2034161 | 7/1991 | Canada | C12Q 1/68 |

OTHER PUBLICATIONS

Rashtchian et al. Anal. Biochem. 206: 91–97, 1992.

Aslanidis and Jong, "Ligation–independent Cloning of PCR Products (LIC–PCR)," *Nucleic Acids Research*, 18(20):6069–6074, 1990.

Higuchi, "Recombinant PCR," *PCR Protocols: A Guide to Methods and Applications*, Academic Press, Inc., Chapter 22, pp. 177–183, 1990.

Hsiao, "Exonuclease III Induced Ligase–free Directional Subcloning of PCR Products," *Nucleic Acids Research*, 21(23):5528–5529, 1993.

Kaluz et al., "Directional Cloning of PCR Products Using Exonuclease III," *Nucleic Acids Research*, 20(16):4369–4370, 1992.

Kuijper et al., "Functional Cloning Vectors for Use in Directional cDNA Cloning Using Cohesive Ends Produced with T4 DNA Polymerase," *Gene*, Elsevier Science Publishers, New York, pp. 147–155, 1992.

Lee et al., "Direct Sequence Analysis of Amplified Dengue Virus Genomic RNA from Cultured Cells, Mosquitoes and Mouse Brain," *Journal of Virological Methods*, 37:275–288, 1992.

Lohff and Cease, "PCR Using a Thermostable Polymerase with 3' to 5' Exonuclease Activity Generates Blunt Products Suitable for Direct Cloning," *Nucleic Acids Research*, 20(1):144, 1991.

Stoker, "Cloning of PCR Products after Defined Cohesive Termini Are Created with T4 DNA Polymerase," *Nucleic Acids Research*, 18(14):4290, 1990.

Yang et al., "Construction of Recombinant DNA by Exonuclease Recession," *Nucleic Acids Research*, 21(8):1889–1893, 1993.

Yang, "NonO, A Non–POU–Domain–Containing, Octamer–Binding Protein, Is the Mammalian Homolog of Drosophila nonA$^{diss}$," *Molecular and Cellular Biology*, 13(9):5593–5603, 1993.

Dialog Search Report dated Nov. 27, 1992.

*Primary Examiner*—Stephanie W. Zitomer
*Assistant Examiner*—Paul B. Tran
*Attorney, Agent, or Firm*—Arnold, White & Durkee

[57] ABSTRACT

An exonuclease-based method for joining and/or constructing two or more DNA molecules. DNA fragments containing ends complementary to those of a vector or another independent molecule were generated by the polymerase chain reaction. The 3' ends of these molecules as well as the vector DNA were then recessed by exonuclease activity and annealed in an orientation-determined manner via their complementary single-stranded regions. This recombinant DNA may be transformed directly into bacteria without a further ligase-dependent reaction. Using this approach, recombinant DNA molecules are constructed rapidly, efficiently and directionally. This method can effectively replace conventional protocols for PCR cloning, PCR SOEing, DNA subcloning and site-directed mutagenesis.

56 Claims, 10 Drawing Sheets

CONSTRUCTION OF RECOMBINANT DNA BY EXONUCLEASE RECESSION

Research leading to the present invention was supported in part by National Institute of Health Awards AI-12127 and GM-31689. The U.S. government therefore has certain rights in the invention.

BACKGROUND OF THE INVENTION

1. Field of the Invention

The present invention relates to the field of molecular biological techniques useful for the construction of recombinant DNA molecules. More particularly, the present invention relates to methods that use bipartite oligonucleotide primer/adapters and exonuclease treatment for the rapid, efficient and directional joining of two or more DNA molecules into any vector at a single restriction site. The field of the invention also relates to PCR subcloning, deletion mutant construction, site-directed mutagenesis, and oligonucleotide site insertion.

2. Related Art

The use of the polymerase chain reaction (PCR) in nucleic acid research has provided a convenient way to amplify and construct recombinant DNA. PCR is an in vitro method of nucleic acid synthesis by which a particular segment of DNA can be specifically replicated. The method involves two oligonucleotide primers that flank the DNA fragment to be amplified and repeated cycles of heat denaturation of the DNA, annealing of the primers to their complementary sequences, and extension of the annealed primers with DNA polymerase. These primers hybridize to opposite strands of the target sequence to form a construct, the primers being oriented so that DNA synthesis by the polymerase proceeds across the region between the primers. Since the extension products themselves are also complementary to and capable of binding primers, successive cycles of amplification essentially double the amount of DNA synthesized in the previous cycle. The result is an exponential accumulation of the target fragment, approximately $2^n$, where n is the number of cycles of amplification performed.

In many applications, the orientation of the DNA fragment in the PCR construct is crucial for gene expression. The incorporation of different restriction enzyme sites into both ends of a PCR product is a common technique used to achieve this goal[1]. However, restriction enzyme cleavage at the ends of PCR products is often inefficient, and in some cases compromised by the presence of internal sites within the insert target DNA.

In most cases, subcloning of PCR products is required for further manipulation. Subcloning of these products generally involves the incorporation of restriction sites at the ends of PCR products[1,2], or blunt-ended ligation of PCR products into the vector[3]. However, cloning of PCR products is often not straightforward.

Several technical problems exist with the use of such techniques. Restriction sites at the ends of PCR products are often inefficiently cleaved by restriction enzymes because they are too close to the end of the DNA fragment. The PCR products lack part of the binding region for the restriction enzyme to contact the DNA template. The introduction of extraneous nucleotides at the 3' end of the amplified DNA fragments by Taq DNA polymerase[3,4] leads to relatively low overall efficiency of the blunt-end ligation reaction. The incorporation of extraneous nucleotides would alter a reading frame and constructs a copy that includes the undesired nucleotide. The efficiency of blunt ended ligation is poor for the following reasons: i) the $K_m$ for the activity of T4 ligase on blunt-ended DNA is nearly 100 times higher than its $K_m$ on DNA with cohesive ends, thus, ligation of blunt-ended DNA requires a high concentration of enzyme and a high concentration of DNA ends (greater than 1 μM), therefore very large amounts of the fragment to be cloned are needed, ii) during blunt-end ligation, a fraction of the plasmid vector will recircularize and contribute to non-recombinant backgrounds, and iii) because of the high concentration of the fragments to be cloned, many recombinant plasmids will contain more than one insert of foreign DNA. Furthermore, blunt ended cloning is directionless.

The T/A cloning system (Invitrogen) has been used to overcome the extra nucleotide problem at the 3' end. However, using this technique, an extra dAMP is automatically inserted. This generates additional problems especially in expression studies, primarily because it will alter the reading frame. Another approach has been to use cohesive end cloning (provided by the incorporation of restriction sites at the 5' end of PCR primers). While this provides an alternative to blunt-end cloning, this and the T/A cloning system require several steps of DNA fragment purification, an overnight ligase-dependent ligation and colony selection to determine the correct orientation of the insert and are labor intensive, time consuming and/or of low efficiency. It will usually take at least one day to prepare DNA fragments and another day for the ligase reaction.

Strategies for ligase-free cloning of PCR products have also been proposed in an attempt to overcome some of these problems. For example, the recombinant circle PCR (RCPCR) technique generates circular DNA through heterologous annealing of sequence-overlapped ends on different PCR products[5,6]. These circular DNA forms can be transformed directly into bacteria without a ligation procedure. However, this method requires either multiple sets of PCR primers or PCR reamplification of sequence-overlapped molecules to splice insert and vector DNA together[7]. Also in these applications, both insert and vector DNA must be amplified. Vector DNA amplification adds to the limitation on the size of the DNA fragment that can be amplified by Taq DNA polymerase.

An alternate strategy is to construct sequence-specific, single-stranded ends on both PCR products of insert and vector ends[8–10], then splice them through a sequence homologous annealing process. In most applications, single-stranded ends are generated by the 3' to 5' exonuclease activity of T4 DNA polymerase[8,9] with the overlapped sequence specifically designed and incorporated into PCR primers for both insert as well as vector DNA amplification. A specified, unique length of 3' recessed ends is then created in the presence of specific dNTP(s) and T4 DNA polymerase, and the circular form of DNA, assembled through sequence overlapped ends, is ready for transformation.

Aslanidis et al.[8] relates to a procedure for preparing recombinant molecules employing PCR products and a PCR-amplified plasmid vector. The procedure includes a step wherein the 3'-terminal sequence is removed by the action of the (3'-5') exonuclease activity of T4 DNA polymerase in the presence of a specific dNTP, providing fragments with 5'-extending single-stranded (SS) tails of defined sequence and length. Therefore, this method is restricted to those vectors which have modified, defined end sequences.

Stoker et al.[9] relates to the cloning of PCR products using the construction of cohesive termini on PCR products using a T4 DNA polymerase. Specifically, T4 DNA polymerase was used to remove 3' terminal sequence in the PCR products thus constructing the cohesive AccI and XmaI termini. In the described reaction, the 3' to 5' exonuclease activity of T4 DNA is to be limited to removal of only bases G and C in order to prepare the desired recessed termini.

Kuijper et al. relates to the preparation of "Prime" cloning vectors. T4 DNA polymerase is employed to produce single-stranded ends of vector and insert DNA in the presence of dTTP and dATP, respectively.

These methods[8,9,20] used to create single-stranded ends by T4 DNA polymerase incorporate specific nucleotide(s) in the reaction to stop exonuclease activity at a nucleotide of specific sequences. Kaluz[10] appears to fix PCR insert ends on two restriction sites which are compatible with vector sites and ligate them together for directional cloning. All of these methods relate to single fragment subcloning, and none of them could be used with chimeric genes or to construct deletion mutants as described in the present invention. This is because, among other reasons, they require either defined end sequences on both insert and vector DNA ends or different restriction sites on the ends of vector and insert DNA for directional cloning.

An alternative way to produce single-stranded ends employs uracil DNA glycosylase (UDG). This enzyme cleaves all dUMPs which are incorporated into the PCR primers[11]. Some of the aforedescribed methods, like RCPCR, require either multiple PCR primer sets, vector amplification, or vector end sequence modifications. Others require a double restriction enzyme cleavage of vector and insert DNA followed by a ligation process for directional cloning[9,10].

Lohff and Cease relates to the use of a 3' to 5' exonuclease to prepare blunt-ended PCR products for non-directional cloning into blunt-cut vectors.

PCR SOEing[14,15] is a relatively useful technique employed to construct gene mutants, fusion genes and chimeric genes. PCR SOEing has also been used for site-directed mutagenesis, as described by Higuchi.[14,21] However, this technique requires at least two sequential PCR amplifications. Since Taq DNA polymerase has a mutation rate of about 0.04%, each time that an amplification round is required, this incorporation of incorrect nucleotides is amplified. In general, PCR SOEing is limited to DNA fragments of about 1 kb or less.

Several protocols utilizing ligase-free ligation of PCR products have been described[5-8,11]. These protocols still have at least one or more of the following disadvantages: vector amplification, vector sequence modification, multiple primer sets and sequential PCR reamplification(s).

Kaluz et al.[10] has reported directional cloning of PCR products without restriction enzyme cleavage of insert DNA fragments. They used a strategy similar to that of Stoker[9] to construct cohesive termini for subcloning. However, both protocols require a ligase-dependent ligation procedure. Other protocols with a ligase-independent procedure require vector amplification to incorporate a specific sequence for annealing[7,8,11]. The Stoker[9], Kaluz[10], RCPCR[5-7] and ligation-independent cloning methods[8,11] do not allow the construction of chimeric products of the PCR 'SOEing' variety for the above-stated reasons.

A need continues to exist for a technique of constructing recombinant DNA molecules that addresses the disadvantages of present techniques, e.g., vector amplification, enzymatic manipulation, lack of directional cloning, insertion of restriction enzyme sites at the ends of PCR products where cleavage is inefficient, sequential PCR amplifications that multiply error and the incorporation of additional nucleotides which changes a reading frame and provides incorrect copies.

ABBREVIATIONS

IPTG: Isopropyl-β-D-thiogalactopyranoside
PCR: Polymerase chain reaction
SOEing: Splicing of overlap extension
PFU DNA polymerase: DNA polymerase from Pyrococcus furiosus

SUMMARY OF THE INVENTION

The present inventors have developed a surprisingly effective exonuclease-based strategy to construct recombinant DNA molecules. This protocol has the advantages of being ligase-free, not requiring vector amplification, vector sequence modification or enzymatic manipulation of either vector or insert DNA and of providing directional cloning at a single restriction site in a vector.

The techniques of the present invention may be used to construct recombinant DNA molecules using virtually any nucleic acid sample that includes at least one intact DNA or RNA strand, or fragment thereof, or at least one intact oligonucleotide strand, that encompasses a region to be amplified and whose impurities are sufficiently dilute so as to not inhibit polymerization.

In general, the present invention provides a method of constructing a recombinant DNA molecule comprising the following steps: 1) obtaining at least two linearized DNA molecules; 2) obtaining at least two bipartite oligonucleotide primer molecules, each having a first portion which primes a PCR extension of a first DNA molecule and a second portion which is complementary to a second DNA molecule; 3) annealing the primer molecules to the first DNA molecule to form a PCR substrate; 4) amplifying the PCR substrate to produce a PCR product; 5) treating the PCR product to form a recessed PCR product; 6) treating the second DNA molecule to form a recessed DNA molecule; and 7) annealing the recessed PCR product to the recessed DNA molecule to form a recombinant DNA molecule. This method may be used to recombine any number of DNA fragments and for each additional fragment incorporated, an additional set of bipartite primers is obtained. The most common application of the present invention is where the first DNA molecule is a template DNA molecule and the second DNA molecule is a vector DNA molecule.

By way of example, the present techniques are particularly useful in the construction of recombinant DNA molecules comprising nucleic acid fragments or oligonucleotides of from between about 12 nucleotides and about 50,000 nucleotides in length. A more preferred range for a target insert nucleic acid is between about 12 and about 10,000 nucleotides. Most preferably, the target nucleic acid molecule will include at least about 24 nucleotides, but not more than about 5,000 nucleotides.

The nucleic acids or oligonucleotide sequences that may be incorporated into a recombinant DNA molecule according to the present technique may be obtained from genomic DNA of prokaryotic or eukaryotic genomes, as well as from various vectors, including plasmids, cosmids, phage, YACs, and the like. Alternatively, the nucleic acid or oligonucleotide may be derived from somatic cells, mitochondria, or chloroplasts. The nucleic acid or oligonucleotide may also be synthesized by automated synthesis and the like. The nucleic acid may also be derived from RNA species, such as mRNA, tRNA, rRNA or others; from any species and may be first converted to cDNA by reverse transcriptase and then amplified (Sambrook et al.[23]).

The quality and quantity of the nucleic acid sample or oligonucleotide sample that may be used in the claimed methods need not be particularly high to realize the high yield of amplified product of the invention. A single cell, or crude lysate prepared by simply boiling cells in water is expected to be useful for successful amplification according to the disclosed methods. A preferred amount of plasmid DNA for amplification is about 100 ng.

The particular advantage of the present invention is the combination of using custom-designed bipartite oligonucleotide primer molecules to generate a PCR product and the use of exonuclease recession to generate complementing single stranded regions on both vector and insert DNA for annealing to form a resultant recombinant molecule (FIG. 1A). This methodology always results in a directional cloning of DNA insert into a single restriction site in a vector. The vector ends may be generated from any restriction enzyme cleavage.

A preferred embodiment of the present invention is a method of constructing a recombinant DNA molecule comprising the following steps: 1) obtaining a linearized vector DNA molecule and a template DNA molecule, each molecule having a first end and a second end, each end having a known sequence of at least about 8 nucleotides; 2) obtaining a first primer DNA molecule having a 3' end complementary to the first end of the template DNA molecule and a second primer DNA molecule having a 3' end complementary to the second end of the template DNA molecule, the first and second primers having 5' ends complementary to the known sequence of the first and second ends of the vector DNA, respectively; 3) annealing the primer DNA molecules to the template DNA molecule to form a PCR substrate; 4) amplifying the PCR substrate to produce a PCR product; 5) treating the PCR product to form a recessed PCR product; 6) treating the linearized vector DNA molecule to form a recessed vector DNA molecule; and 7) annealing the recessed PCR product and the recessed vector DNA molecule to form a recombinant DNA molecule.

Preferably, the template DNA molecule has at least two known sequences of between about 8 to about 20 nucleotides, and most preferably, the template DNA molecule has at least two known sequences of about 12 nucleotides. The template DNA molecule may comprise two molecules of DNA, each molecule having a first end and a second end with known sequences of between about 8–20 nucleotides. In a further embodiment, the template DNA molecule may comprise a region to be deleted and further known sequences are flanking the region to be deleted. In particular, the template DNA molecule is a molecule of DNA containing the nonO gene, the phosphoducing gene, the calreticulum gene promoter sequences, the TAP1 gene, an oligonucleotide, an oligonucleotide containing a viral proteinase cleavage site, or an oligonucleotide containing a histidine tag.

The template DNA molecule may comprise a sense and an antisense strand, and in that case, the first primer DNA molecule may be complementary to a portion of the sense strand and the second primer DNA molecule may be complementary to a portion of the antisense strand. Alternatively, the first primer DNA molecule may be complementary to a portion of the antisense strand and the second primer DNA molecule may be complementary to a portion of the sense strand.

A further step of adding a nucleotide residue to a primer DNA molecule to form an extended primer DNA molecule before the first annealing step is an aspect of the present inventive method if it is needed. This added nucleotide may be desired to construct a proper reading frame for an expression vector. One skilled in the art would realize that 2 nucleotides may need to be added to achieve a proper reading frame. In particular, the vector DNA molecule may be pGEX-KG and the method includes the step of adding a dAMP residue to the second primer DNA molecule to form an extended second primer DNA molecule before the first annealing step.

A primer as used in the description of the present invention is defined as a bipartite primer, i.e., a primer having two (a first and a second) portions (FIG. 1A and 1B). A first portion of the primer is designed to prime a PCR reaction on a template strand of a first DNA molecule and a second portion of the primer is designed to anneal to a second DNA molecule. The region of the first DNA molecule for priming and the second DNA molecule for annealing will usually be at the ends or near the ends of these DNAs, but also may be internally located in the DNA molecules, especially for the construction of deletion mutant molecules. While the examples provided use two or four bipartite primers, one skilled in the art of recombinant DNA technology would see that 3, 4 or more fragments of DNA may be recombined by the present methods. For each additional fragment, an additional set of bipartite primers is obtained as shown in FIG. 7. The primer 'M' and primer '3' of FIG. 7 may be bipartite or monopartite to save on oligonucleotide synthesis expenses. The number of fragments that may be incorporated depends on the size of the DNA fragments which the vector and host cell can tolerate.

The bipartite oligonucleotide primer/adapters of the present invention may be broadly defined as single stranded oligonucleotides that are complementary to DNA molecules of interest, and in the present inventive method, allow the DNA molecules to be efficiently incorporated into a vector. Bipartite primers will generally have a minimum length of about 16 nucleotides and a maximum length of about 40 nucleotides. A more preferred length range of a primer is between about 17 and about 33 nucleotides.

The sequence of the primer will be dictated by the particular DNA fragments to be recombined. Generally, an area of template DNA having high GC content is chosen since GC base pairs have three hydrogen bonds and therefore are more strongly bonded than AT base pairs which have only two hydrogen bonds. When an area of a DNA fragment having a high AT content must be used for annealing, then a primer is designed which is longer in order to enhance the specificity of annealing. The degree of strength of an annealed DNA duplex is frequently described by a $T_m$ value, i.e., a melting temperature which is the midpoint of the temperature range over which the strands of DNA separate. A $T_m$ of 30°–37° C. is usually chosen herein for the annealing process and 60°–70° C. for the PCR priming process. For a rough estimate of $T_m$ values, each G or C nucleotide contributes 4° C. and each A or T nucleotide contributes 2° C. to the $T_m$ of an oligonucleotide. This simple formula works for oligonucleotides having a length from about 4 to 30 nucleotides.

The exonuclease activity used to recess the ends of a PCR product to form a recessed PCR product or to recess the ends of a linearized vector is a strand-specific exonuclease such as the 3' to 5' exonuclease activity of T4 DNA polymerase or Exonuclease III. A 5' to 3' exonuclease activity would also work in the present invention. An advantage of the present invention is illustrated in that when recessing ends with an exonuclease activity, nucleotides are not included in the reaction mixture, and the activity is not stopped at a specific nucleotide on the template DNA.

The present invention provides methods for constructing chimeric genes for virtually any protein for which at least part of the nucleic acid sequence is known or may be deduced using techniques known to those of ordinary skill in the art (FIG. 4). Another preferred embodiment is a method of constructing a recombinant DNA molecule of a first and a second DNA molecule, each molecule having known sequences of at least about 8 nucleotides. The method comprises the steps of: 1) obtaining a linearized vector DNA molecule, a first and a second DNA molecule, each molecule having a first end and a second end; 2) obtaining a first primer DNA molecule having a 3' end complementary to the first end of the first DNA molecule and a 5' end complementary to the first end of the linearized vector DNA molecule; 3) obtaining a second primer DNA molecule having a 3' end complementary to the second end of the first DNA molecule and a 5' end complementary to the first end of the second DNA molecule; 4) obtaining a third primer DNA molecule complementary to the first end of the second DNA molecule; 5) obtaining a fourth primer DNA molecule having a 3' end complementary to the second end of the second DNA molecule and a 5' end complementary to the second end of the linearized vector DNA molecule; 6) annealing the primer molecules to the first and the second DNA molecules to form PCR substrates; 7) amplifying the PCR substrates to produce PCR products; 8) treating the PCR products to form recessed PCR products; 9) treating the linearized vector molecule to form a recessed vector molecule; and 10) annealing the recessed PCR products and the recessed vector molecule to form a recombinant molecule of a first and a second DNA molecule. The first and second DNA molecules may be separate molecules or they may be nonoverlapping fragments of one molecule. In particular aspects of the invention, the technique is exemplified in constructing bacterial gene fusion mutants for an octamer binding protein[12], the NonO gene, phosphoducing gene, calreticulum gene promoter sequences, TAP1 gene and oligonucleotides with a TEV viral proteinase cleavage site and an oligomer of histidine tag.

The present invention provides an elegant, simplified solution to problems associated with conventional nucleic acid cloning techniques aforedescribed. Essentially, different DNA fragments may be linked by annealing sequence complementary single-stranded ends. Since the end sequence of each DNA fragment is unique, two or more DNA fragments may be spliced in a defined orientation without manipulating restriction enzyme sites. Endonuclease cleavage is only required to linearize the vector DNA. According to the present invention, vector DNA does not require a second restriction enzyme cleavage for directional cloning or dephosphorylation of the ends to reduce vector background. After annealing the DNA inserts with vector, the recombinant circular DNA is introduced into a transformable host without further ligation.

The efficiency of this method, while generally improved over techniques currently employed, will vary depending on the intrinsic properties of the insert DNA. Generally for 0.5 μg of vector DNA and PCR fragments, approximately between about 50 to about 200 colonies will grow in the selection medium. A particular advantage of the method is that T4 DNA polymerase treated vector DNA gives a very low background after transformation into host cells (occasionally one or two colonies may be present). Theoretically higher efficiencies could be achieved with extended incubation times during annealing. One of the advantages of the present invention is that the efficiency of the method is increased 100% over cloning methods that are non-directional, i.e., the method is selective for the correct orientation of insert DNA. Therefore, host cells that have been transformed by a recombinant vector will have the insert DNA in the correct orientation in that vector.

By using the protocol described herein, recombinant DNA molecules with 2 or more DNA fragments may be constructed in a unique and desired orientation in a single annealing step (FIGS. 4 and 7). For these DNA fragments only one PCR reaction is required to synthesize appropriate DNA fragments for insertion into recombinant DNA molecules. Neither PCR reamplification of the PCR products nor restriction enzyme cleavage for cohesive end-cloning of the final DNA products is required in any of these applications. Any mutation caused by Taq DNA polymerase[16] is therefore limited to the first reaction, and a theoretical reduction of the error by at least 50% provides a significant advantage over PCR SOEing. Taq DNA polymerase is preferred, however, Vent DNA polymerase or PFU DNA polymerase may also be used for the amplification step.

The overlapping, annealing sequence incorporated into the 5' end of PCR primer 2 (FIG. 4) exists in target DNA 2. Therefore, no additional nucleotides are introduced into the spliced constructs and there are neither changed nor additional amino acid(s) at the junctions. This advantage is true for all the applications of the invention (FIGS. 1A, 4, 5, 6 and 7), unless a nucleotide was intentionally added. For PCR amplification conditions, fewer cycles are preferred (e.g. about 20 cycles, instead of the more usual 30–35 cycles). High concentrations of template (about 100 to about 200 ng) to further reduce the potential mutations incorporated by Taq DNA polymerase is also most particularly preferred in the amplification step of the invention, primarily to yield more product because fewer cycles are desired in the amplification step. Using these conditions, no sequence errors were detected in clones generated using this technique.

A further preferred embodiment of the present invention is a method of constructing a recombinant DNA molecule from at least four DNA molecules, each molecule having known end sequences of at least about 8 nucleotides (FIG. 7). The method comprises the steps of: 1) obtaining a linearized vector DNA molecule, a first and a second DNA molecule, each molecule having a first end and a second end; 2) obtaining at least one internal DNA molecule having a first end and a second end; 3) obtaining a first primer DNA molecule having a 3' end complementary to the first end of the first DNA molecule and a 5' end complementary to the first end of the linearized vector DNA molecule; 4) obtaining a second primer DNA molecule having a 3' end complementary to the second end of the first DNA molecule and a 5' end complementary to the first end of at least one internal DNA molecule; 5) obtaining a primer DNA molecule complementary to the first end of at least one internal DNA molecule; 6) obtaining a primer DNA molecule having a 3' end complementary to the second end of at least one internal DNA molecule and a 5' end complementary to the first end of another internal DNA molecule; 7) obtaining a primer DNA molecule having a 3' end complementary to the second end of at least one internal DNA molecule and a 5' end complementary to the first end of the second DNA molecule; 8) obtaining a third primer DNA molecule complementary to the first end of the second DNA molecule; 9) obtaining a fourth primer DNA molecule having a 3' end complementary to the second end of the second DNA molecule and a 5' end complementary to the second end of the vector DNA molecule; 10) annealing the primer molecules to the first, the second and the internal DNA molecules to form PCR substrates; 11) amplifying the PCR substrates to produce PCR products; 12) treating the PCR products to form recessed PCR products; 13) treating the linearized vector molecule to form a recessed vector molecule; and 14) annealing the recessed PCR products and the recessed vector molecule to form a recombinant molecule from at least four DNA fragments; wherein the four DNA fragments include a vector molecule, a first DNA molecule, a second DNA molecule, and an internal DNA molecule. The first, the second or the internal DNA molecule may have a length from about 12 to about 50,000 nucleotides, or preferably, from about 12 to about 10,000 nucleotides, or more preferably, from about 24 to about 5,000 nucleotides. The recombinant molecule may be constructed from four DNA molecules.

The described strategies can be applied to perform site-directed mutagenesis (FIG. 5). For example, a pair of oligomers, primer 2 and primer 3, containing an internal mutated sequence may be used as PCR amplification primers. The mutant gene may be assembled as described for the construction of internal deletions or chimeric genes (FIGS. 4 and 7, as described above). A method of constructing a site-directed mutation in a recombinant DNA molecule comprises the steps of: 1) obtaining a template DNA molecule having a first end, an internal region for mutation and a second end, each end having a known sequence of at least about 8 nucleotides and the internal region for mutation having a known sequence of at least about 16 nucleotides; 2) obtaining a linearized vector DNA molecule having a first end and a second end, each end having a known sequence of at least about 8 nucleotides; 3) obtaining a first primer DNA molecule having a 3' end complementary to at least about 8 nucleotides of the known sequence of the first end of the template DNA molecule and a 5' end complementary to at least about 8 nucleotides of the known sequence of the first end of the vector DNA molecule; 4) obtaining a second primer DNA molecule having a 3' end complementary to at least about 8 nucleotides of a region 5' to the internal region for mutation of the template DNA molecule, a mutation region, and a 5' end complementary to at least about 8 nucleotides of a region 3' to the internal region for mutation of the template DNA molecule; 5) obtaining a third primer DNA molecule having a 3' end complementary to at least about 8 nucleotides of a region 3' to the internal region for mutation of the template DNA molecule, a mutation region complementary to the mutation region of the second primer DNA molecule and a 5' end complementary to at least about 8 nucleotides of a region 5' to the internal region for mutation of the template DNA molecule; 6) obtaining a fourth primer DNA molecule having a 3' end complementary to at least about 8 nucleotides of the known sequence of the second end of the template DNA molecule and a 5' end complementary to at least about 8 nucleotides of the known sequence of the second end of the vector DNA molecule; 7) annealing the primer molecules to the template molecule to form a PCR substrate; 8) amplifying the PCR substrate to produce PCR products; 9) treating the PCR products to form recessed PCR products; 10) treating the linearized vector molecule to form a recessed vector molecule; and 11) annealing the recessed PCR products and the recessed vector molecule to form a site-directed mutation in a recombinant DNA molecule. The mutation region of the second primer may contain an insertion, deletion or substitution of at least one nucleotide.

In the presently disclosed methods, recombinant DNA molecules are constructed by annealing single-stranded cohesive termini, without the requirement of a ligase-dependent ligation procedure to attain directional cloning, and without the necessity of vector amplification or vector sequence modification. More importantly, the cohesive ends created are not restricted to any defined sequence. Therefore, two or more independent PCR fragments may be spliced together without PCR reamplification, to provide a chimeric gene product. This is accomplished without actually 'SOEing' the fragments by the second PCR reamplification,[14,15] as is typical of other techniques. The Stoker[9], Kaluz[10], RCPCR[5–7] and ligation-independent cloning methods[8,11] do not allow the construction of chimeric products of the PCR 'SOEing' variety. None of the previously described protocols can achieve this objective without PCR reamplification.

A further aspect of the invention is the directional cloning of an oligonucleotide DNA fragment into a single restriction site (FIG. 6). This particular method of constructing a recombinant DNA molecule containing an oligonucleotide fragment comprises the steps of: 1) obtaining a linearized vector DNA molecule having a first end and a second end, each end having a known sequence of at least about 8 nucleotides; 2) treating the linearized vector DNA molecule to form a recessed vector DNA molecule; 3) preparing a double stranded oligonucleotide having single stranded ends of at least 8 nucleotides of known sequence; 4) reacting the double stranded oligonucleotide in a kinase reaction to form a phosphorylated double stranded oligonucleotide; and 5) annealing the phosphorylated double stranded oligonucleotide and the recessed vector DNA molecule to form a recombinant DNA molecule containing an oligonucleotide fragment. The duplex oligonucleotide having single stranded ends complementary to the ends of a vector molecule may have a length of from about 10 to about 100 nucleotides, or more preferably, from about 30–50 nucleotides. Oligonucleotide inserts of lengths less than about 30–50 nucleotides are preferably phosphorylated before the annealing step.

Any vector capable of replicating in a prokaryotic or eukaryotic cell is usable with the present invention, such as plasmids, cosmids, phage, YACs and the like. The vector may be a cloning or expression vector, it may be a prokaryotic (lambda phage, M13 phage, pACYC, pBR, pUC, $\phi$X, T4, T7 and the like) or eukaryotic vector (SV40, YEP, YIP, YRP and the like). Vector molecules that have been used with the invention include pGEX-KG and pGEM-7Z-CAT, linearized with EcoR1 and Bam H1, respectively. The vector may be linearized by a single restriction enzyme cleavage or a double restriction enzyme cleavage. Preferably, the linearized vector DNA molecule has a known sequence of about 12 nucleotides on at least one end.

The present inventive methods may be described as providing for ligation-free, directional cloning of PCR products without specific end sequences. Besides the simplicity of subcloning PCR products, the present methodology has extraordinary advantages for chimeric gene construction and allows the splicing of several different DNA fragments together in a single step reaction (see FIGS. 4, 5, and 7).

A further embodiment of the present invention is a recombinant DNA molecule made by any of the above-described methods.

BRIEF DESCRIPTION OF THE DRAWINGS

FIG. 1A shows the strategy for PCR subcloning. The hatched boxes represent vector sequences. Identical hatch directions within boxes indicates sequence complementarity. The narrow part on the box represents single-stranded DNA, created initially for the vector by restriction enzyme cleavage, and then for both vector and insert, by T4 DNA polymerase recession. Details of cloning and other methods are described in the examples. FIG. 1B demonstrates the complementary sequences of PCR primers 1 and 2. The 5' end bases complementary to the vector ends are marked. Solid bars represent the PCR priming portion and arrows indicate the direction of DNA polymerization. Stars in primer 2 represent the stop codons incorporated.

FIG. 3A provides a Coomassie stain of bacterial fusion proteins. E. coli expressed fusion protein was affinity purified[13] and analyzed on a 10% SDS-PAGE gel. Labels over lanes correspond to the constructs shown in FIG. 2. Arrowheads denote the predicted size of authentic fusion proteins. FIG. 3B shows a Western blot analysis of expressed proteins. A gel prepared identically to that in FIG. 3A was transferred to a PVDF membrane and probed with a rabbit polyclonal antibody specific for the nonO protein[12].

DETAILED DESCRIPTION OF THE PREFERRED EMBODIMENTS

Figure 1A:
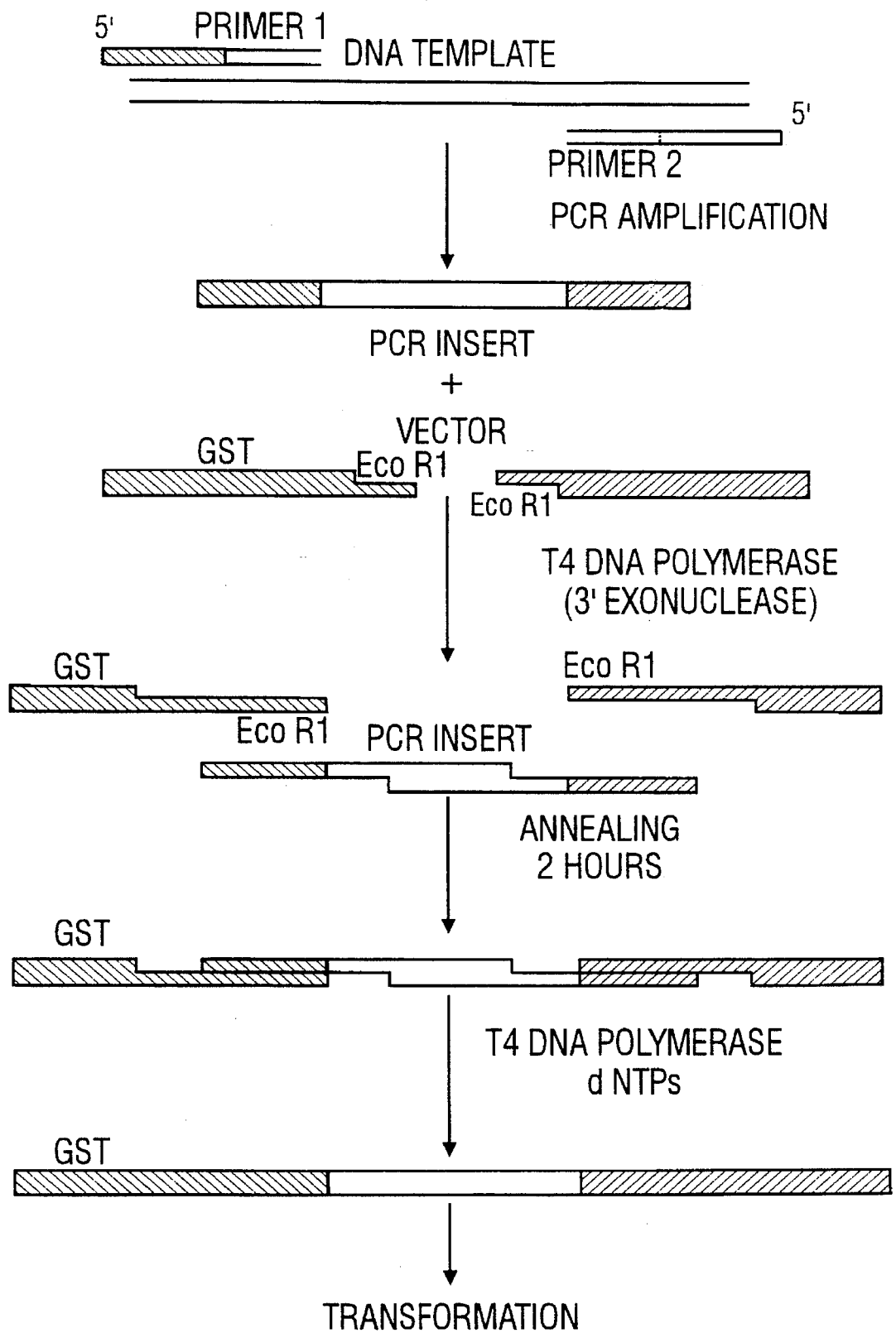
FIGS. 1A and 1B depict the construction of recombinant DNA by exonuclease recession.

The most preferred aspects of the claimed methods involve at least two steps. The first step utilizes bipartite oligonucleotide primer/adapters. In the most common application, one portion of the oligonucleotide primer/adapter primes the PCR extension of one DNA molecule or has sequence homology to the ends of a DNA fragment, and the other portion of the oligonucleotide primer/adapter is complementary to a second DNA molecule. Unlike previously reported protocols[8,9,11], no extra specific sequences are incorporated at the ends of the insert and vector DNA fragments. The second step utilizes exonuclease to generate unique ends. The DNA segments are recessed at the ends by a controlled, strand-specific exonuclease reaction (e.g. the 3' exonuclease activity of T4 DNA polymerase manifested in the absence of dNTP incorporation). After single-stranded overhang ends are created, such DNA molecules of insert and vector are annealed via the complementary bases to form recombinant circular DNA. The remaining gaps are optionally filled in with deoxynucleotide triphosphates, using a T4 DNA polymerase or Klenow fragment of DNA polymerase, and the closed circles are transformed into a host, such as a bacterial host. Any variety of cell that is transformable may serve as a host cell. Examples include E. coli XL1-blue, DHSα, HB101, JM101, JM103, JM109, etc. Other bacterial hosts may include Bacillus or Pseudomonas species and the like. By way of example, eukaryotic host cells may include Saccharomyces species.

The examples provided herein demonstrate how the method may be applied to PCR subcloning, deletion mutant construction and site directed mutagenesis. In examples 1–4, the target molecule is a 2.7 kb cDNA of nonO, an octamer DNA binding protein cloned from mouse B cells[12]. The vector molecule is pGEX-KG, a glutathione-S-transferase encoding bacterial expression vector[13].

The invention may employ any variety of target nucleic acid molecule and any number of inserts. The only limitation on size is the capacity of the vector molecule to carry the insert in transformation and replication in the host cell. DNA fragments that are exemplified in the following examples include: NonO gene (about 300 to 1500 base pairs), phosphoducing gene (about 700 bp), calreticulum gene promoter sequences (about 120 bp), TAP1 gene (about 1 kb) and oligonucleotides with viral proteinase cleavage site (33 bp) and the oligomer of histidine tag (30 bp).

The following examples are provided to satisfy best mode requirements, and are not to be constructed as limiting the scope of the invention. Other modifications and applications of the invention are encompassed within the spirit of the intended invention. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

It is understood that the examples and embodiments described herein are for illustrative purposes only and that various modifications in light thereof will be suggested to persons skilled in the art and are to be included within the spirit and purview of this application and scope of the appended claims.

EXAMPLE 1

Construction of Recombinant DNA by Exonuclease Recession

The present example is provided to demonstrate the utility of the present methods for generating recombinant DNA molecules of a nucleic acid with at least a partially known terminal end sequence by exonuclease recession.

Reagents were obtained from the following sources: T4 DNA polymerase, T4 polynucleotide kinase, and the femtomole sequence kit were from Promega, Madison WI; T4 ligase was from New England Biolabs, Beverly Mass.; dNTPs were from Pharmacia; and reagent grade chemicals were from Sigma, St. Louis, Mo. Vent DNA polymerase may be obtained from New England Biolabs and PFU DNA polymerase may be obtained from Stratagene Cloning Systems, La Jolla, Calif.

Vector DNA, pGEX-KG, was linearized at the single EcoRI restriction site, and gel purified. Approximately 100 ng of template DNA was amplified using a standard polymerase chain reaction for 30 cycles and the PCR products chloroform extracted and salt precipitated. Approximately 0.5 µg of linearized vector DNA and PCR amplified DNA(s) were mixed with 1 unit of T4 DNA polymerase (Promega) in the absence of dNTPs at 37° C. for 2 min in 20 µl of 33 mM Tris-acetate (pH 7.9) containing 66 mM KOAc, 10 mM Mg (OAC)$_2$, 0.5 mM DTT and 100 µg/ml BSA. Following enzyme inactivation at 70° C. for 10 min, the mixture was cooled to annealing temperature as determined by the $T_m$ value of each overlapped sequence region. Generally the temperature of about 30° C. to 37° C. was chosen and mixtures were held at that temperature for at least 2 hrs. One µl of 2 mM dNTPs, 1 µl of 10 mM DTT and another 2 units of T4 DNA polymerase were added and the reaction mixture kept at the annealing temperature for an additional 30 min. Then without a ligation step, the circularized DNA was directly transformed into competent XL1-blue cells (Stratagene Cloning Systems, La Jolla, Calif.) without further manipulation. Individual colonies were randomly selected from each construct for the following expression studies. The fusion proteins were induced with 0.2 mM IPTG for 1 hr. before the cells were harvested and the proteins purified by binding to glutathione agarose beads as described[13]. SDS-PAGE and Western blot analyses were as described previously[12].

Figure 1B:
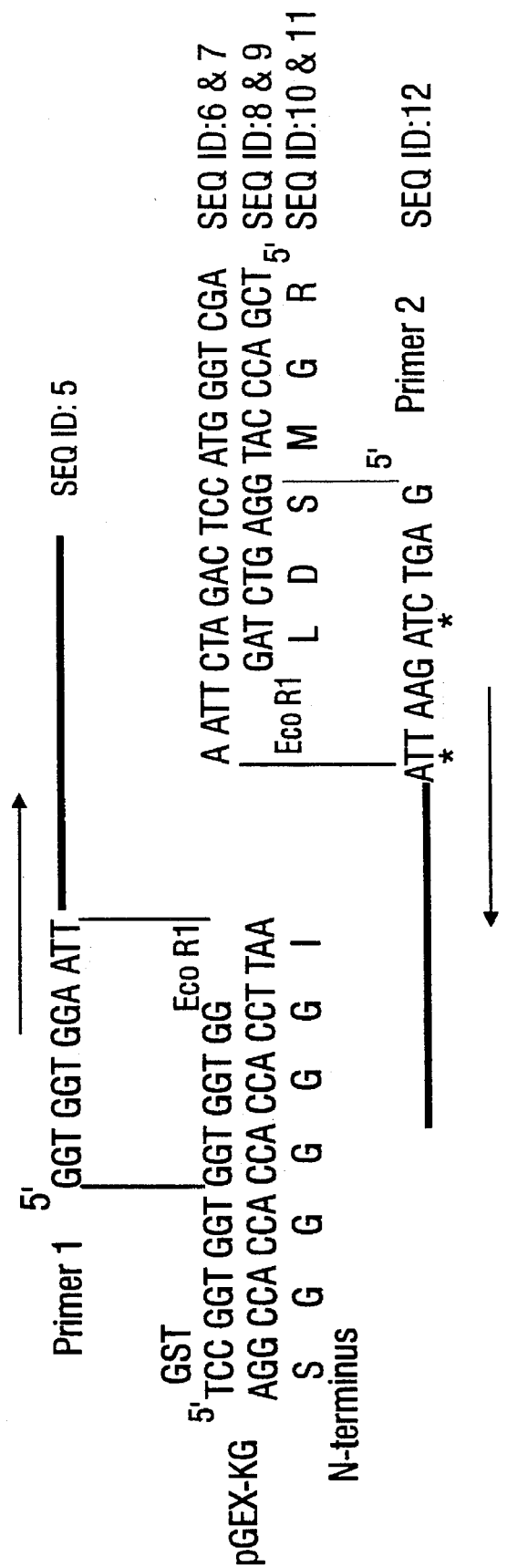

FIG. 1A summarizes the steps involved in the protocol. Primers 1 and 2 are for PCR amplification. The length chosen for primers 1 and 2 depends on the GC content in the sequences used for priming. Generally a primer length with a $T_m$ value of about 60° C. to 70° C. was employed. Each GC pair contributes 4° and each AT pair contributes 2° to the $T_m$ of a primer. The 3' end of each primer is complementary to the end of the target DNA, and the most 5' 10–12 nucleotides are complementary to sequences on each side of the EcoRI cloning site of pGEX-KG. The total length of primer 1 and 2 are 33 and 34 oligonucleotides. A detailed view of the primer-substrate complementarity is shown in FIG. 1B. An additional dAMP was introduced into primer 2 following the vector sequence to construct two in-frame stop codons for the constructed genes. Thus the PCR product obtained from these primers incorporates unique vector end sequences on each of its defined ends. This addition is especially useful for expression vector cloning when the reading frame of the insert is critical.

Thirty cycles of standard PCR were carried out, then a controlled strand-specific exonuclease reaction (the 3' to 5' exonuclease activity of T4 DNA polymerase in the absence of dNTPs) was applied to both PCR product and vector DNA. With a DNA to enzyme ratio recommended by the manufacturer (Promega) and a short reaction time of 2 minutes at 37° C., the T4 DNA polymerase recessed the 3' ends beyond the overlapped sequence regions, but did not degrade the DNA fragments extensively (FIG. 1A).

After the construction of single-stranded complementary ends, recombinant circular DNA molecules were generated by annealing together the insert and vector DNAs for two hours at the annealing temperature which is determined by its Tm value. The remaining single-stranded gaps were filled-in by T4 DNA polymerase (alternatively, Klenow could be used) by adding dNTPs to the reaction. It has been reported that single-stranded gaps of up to 19 nucleotides do not alter transformation efficiency[6]. Therefore, this step may be eliminated from the method without sacrificing transformation efficiency. However, the fill-in steps serve an additional purpose of blunt-ending the non-annealed vector molecules. This eliminates their recircularization by self-annealing and reduces transformation background.

EXAMPLE 2

Exonuclease Recession for Generating Truncation Mutants

The present example is provided to demonstrate the utility of the present methods for generating truncation mutants of virtually any gene. The detailed strategy and protocols to generate these mutants are as described in Example 1. The starting point and ending point of amino acid locations for truncated nonO mutants are labeled in FIG. 2 and the sequence of the primers used for termination are marked with an asterisk in primer 2 of FIG. 1B.

Figure 2:
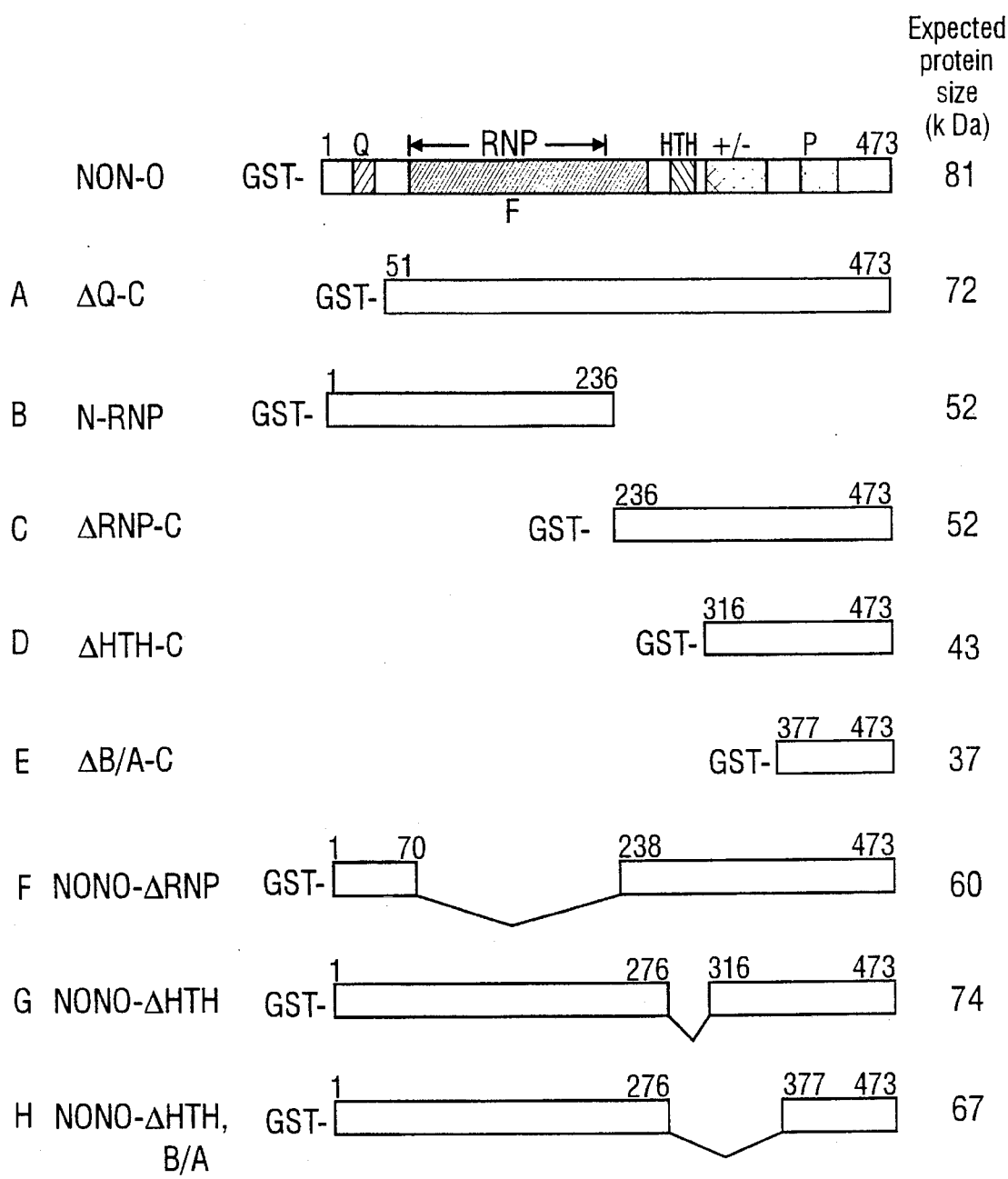
FIG. 2 shows NonO truncation and deletion mutant constructs[24]. Open boxes for all clones represent individual PCR products. The cloning strategies are illustrated in FIG. 1 (clones A–E) and FIG. 4 (clones F–H). Domains marked on the nonO protein are as described previously[12]. The glutathione-S transferase gene was linked at the 5' end of each individual clone.
Figure 3A:
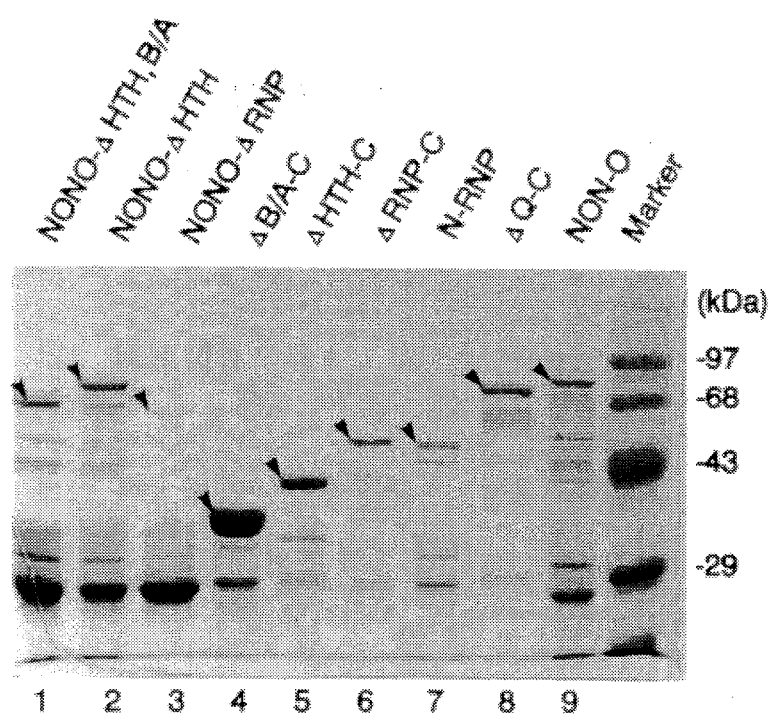
FIGS. 3A and 3B demonstrate verification of constructs by bacterial expression.
Figure 3B:
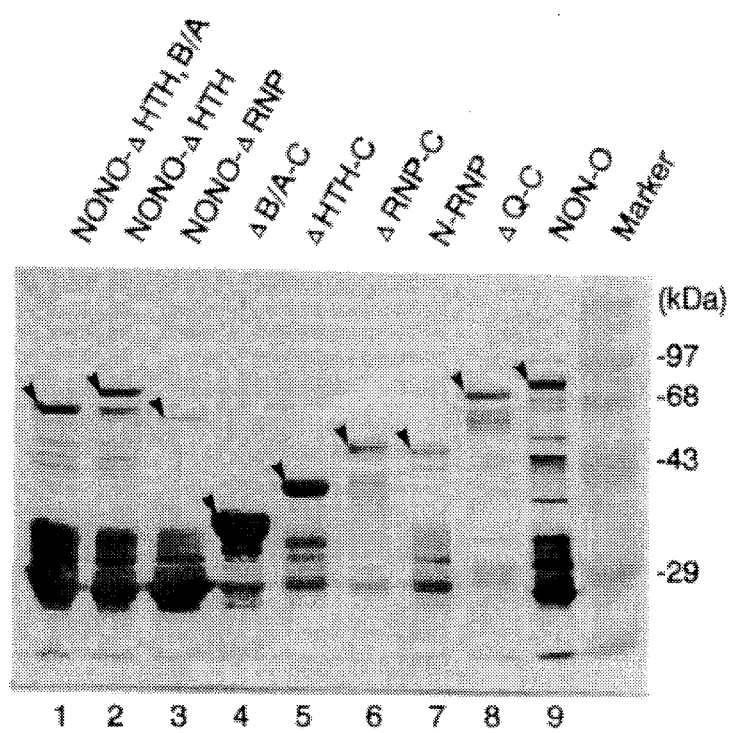

Examples of nonO truncation mutants generated by this method are shown in FIG. 2 (A–E)[12,24]. All of these glutathione-S transferase fusion proteins were expressed in E. coli and migrated at the predicted size on an SDS-PAGE gel (FIG. 3A). Western blot analysis indicated that each mutant retained serologic epitopes, confirming that the appropriate translation frame was maintained (FIG. 3B). DNA sequencing through the junction regions of these clones (data not shown) showed that no nucleotides were lost or gained during the joining process.

EXAMPLE 3

Exonuclease Recession for Generating Internal Deletion Mutants and Chimeric Genes The present example is provided to demonstrate the utility of the present inventive techniques in the construction of internal deletion mutants. These constructs are expected to have particular application in the replacement of the PCR SOEing technique.

Figure 4:
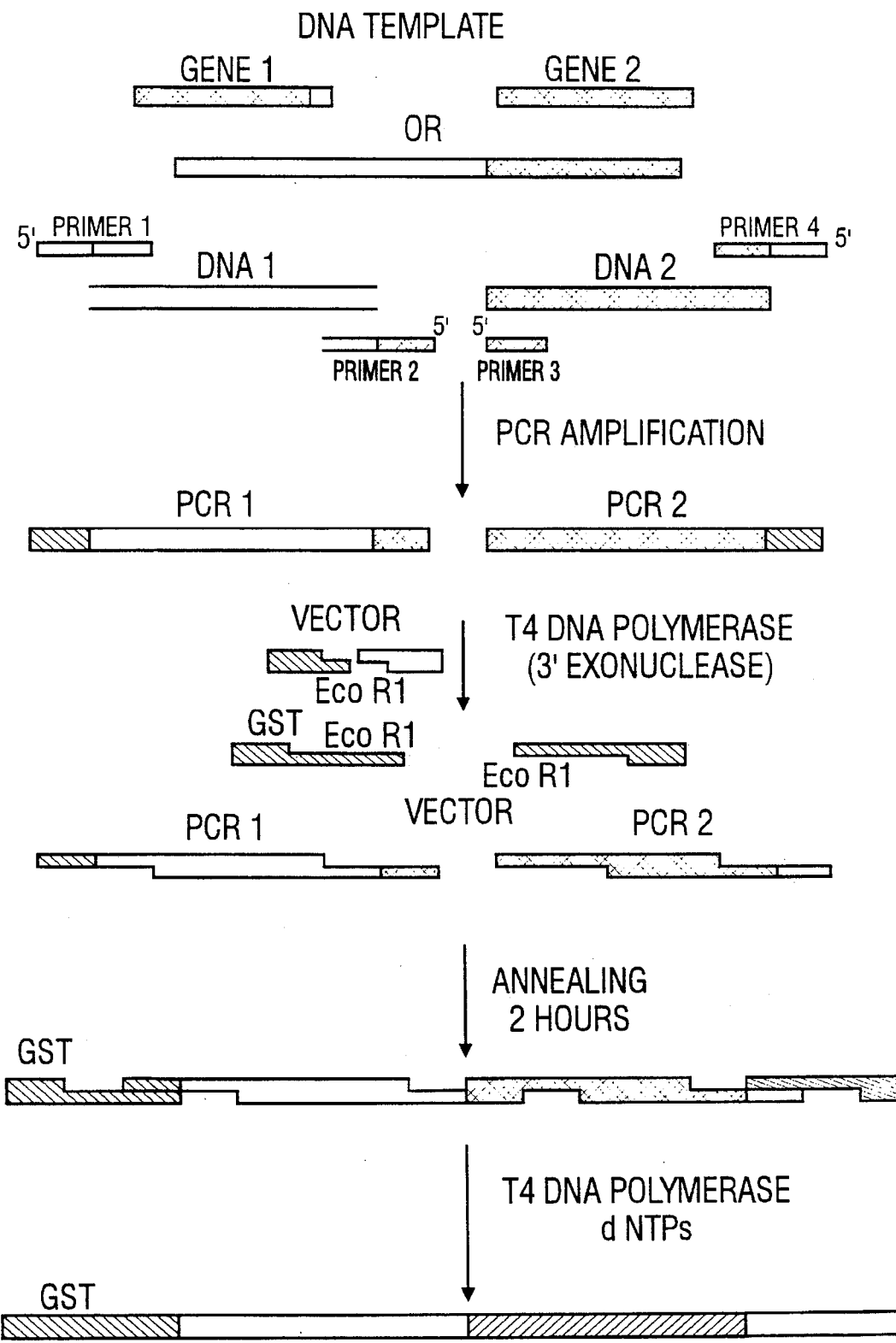
FIG. 4 shows the construction of internal deletions or chimeric genes by exonuclease recession. Primers were designed as discussed in the text (p. 13, line 25 to p. 14, line 24). All symbols correspond to those in FIG. 1A.

As with PCR SOEing, the present methods for generating internal mutations (e.g., fusions, insertions, or deletions) conceptually requires two target DNA molecules (FIG. 4). However, unlike standard SOEing protocols, the present invention does not require multiple reamplification rounds, thus decreasing the probability of Taq polymerase induced mutations. In addition, the present techniques do not have the serious size limitations known to limit the use of standard protocols, thus enhancing the scope of potential uses of the present invention.

For deletion and insertion mutants, target DNA 1 and 2 use the same template, that is, they are part of the same molecule; for chimeric fusions, DNA 1 and 2 use different templates, that is, they are different molecules. The protocol shown in FIG. 4 illustrates internal deletions or chimeric gene construction. Two oligonucleotide primers were designed for each PCR amplification. Primers 1 and 4 were designed using the same strategy as for PCR subcloning. Primer 2 has a 12 nucleotide overlap with target DNA 2 at its 5' end. The 3' half of primer 2 and all of primer 3 are complementary to the boundary specified (in this case, at the breakpoints of the deletion). A preferred primer overlap may be from about 9 to about 15 nucleotides. The design of primers 2 and 3 determine the extent of the deletion down to a specific nucleotide based on whether the complementing nucleotide is incorporated into the primer or not.

All of the primers were designed to maintain the original reading frame in deletion constructs. Following the PCR reaction that generated DNA fragments PCR1 and PCR2 as described in Example 1, 0.5 µg of EcoRI digested pGEX-KG vector DNA was added, and then all three DNA fragments were recessed with T4 DNA polymerase as described in Example 1. The recessed heteroduplexes were assembled via annealing of homologous overlapped end sequences. Through this process, recombinant circular molecules of defined orientation were ready for transformation without further manipulation or purification.

Examples of nonO deletion mutants constructed in this way are shown in FIG. 2 (F–H). Western blot analysis (FIG. 3A and 3B) and DNA sequencing confirmed that the hybrid proteins were authentic.

EXAMPLE 4

Exonuclease Recession for Construction of Site-Directed Mutants

Figure 5:
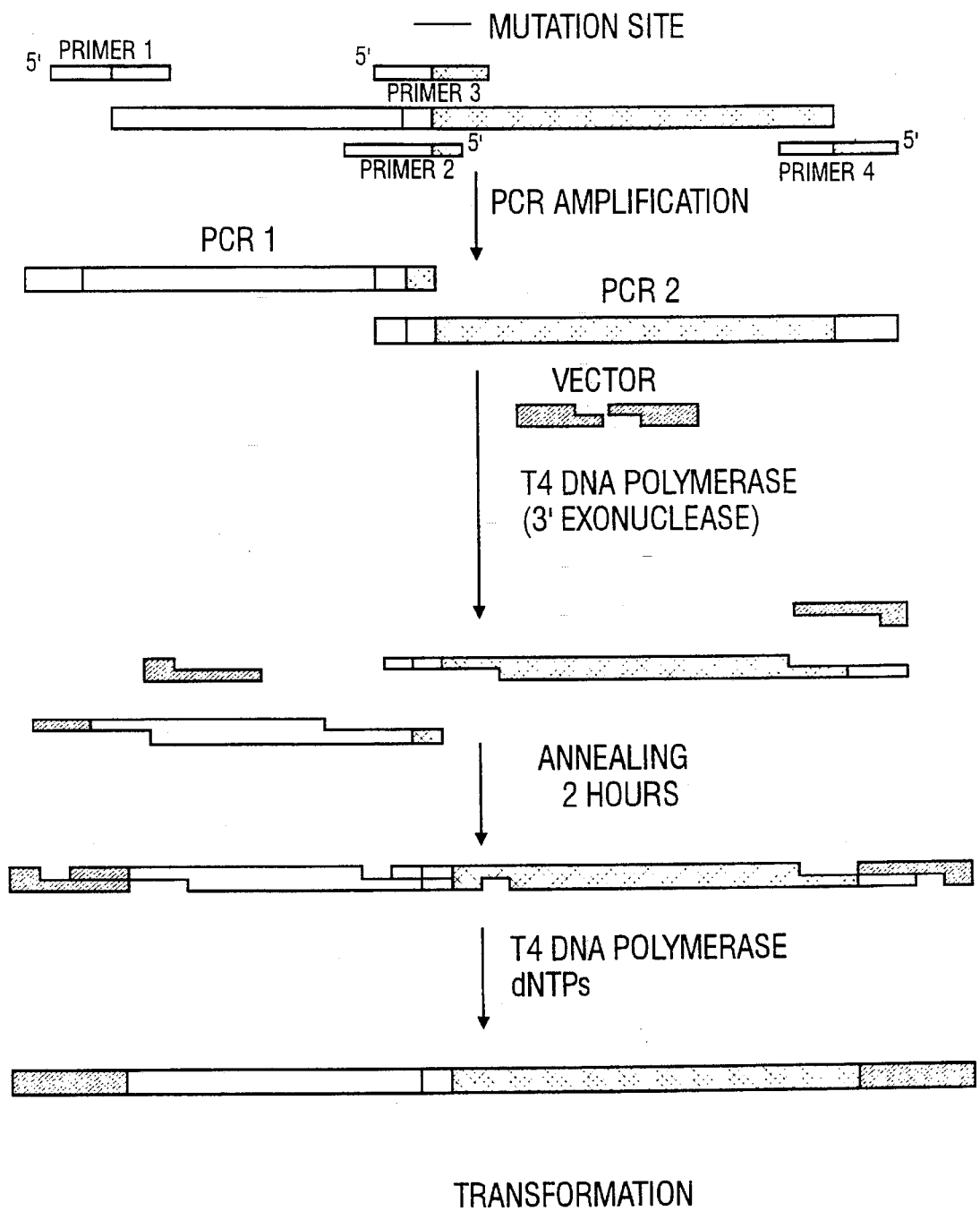
FIG. 5 shows the construction of site-directed mutations by exonuclease recession. A designated mutated site (open box) can be incorporated into primers 2 and 3. All other symbols are as in FIG. 1A.

The present exonuclease recession method may be used for construction of site-directed mutations. An example of this technique is provided in the results as demonstrated in FIG. 5. The mutation may be an insertion, a deletion or a substitution of one or more bases. A designated mutated site is indicated as an open box in FIG. 5 and is incorporated into primers 2 and 3. Once the primers are synthesized, the rest of the procedure is as in Example 1. PCR amplification followed by exonuclease recession of PCR products and vector DNA results in DNA fragments that, when annealed, form a recombinant DNA molecule having the designated mutated site (see FIG. 5). The mutation introduced into this product is therefore the result of the particular deletion, insertion or substitution designed into the primer(s) of the herein described methods.

EXAMPLE 5

Bipartite Oligonucleotide Primers/Adapters

The bipartite oligonucleotide primer/adapters of the present invention may be broadly defined as single stranded oligonucleotides that are complementary to DNA molecules of interest, and in the present inventive method, allow the DNA molecules to be efficiently incorporated into a vector. The bipartite oligonucleotide primer/adapters are custom designed for the particular application, the particular vector and particular insert DNA of interest, to be employed in the use of the herein-described methods. The nucleotide sequence of about 8–20 bases on both sides of a unique restriction enzyme site of a vector should preferably be known for the design of the 5' end of the bipartite oligonucleotide. However, where fewer bases are known, the annealing temperature may be lowered to allow annealing of shorter ends. Preferably the sequence of about 10–12 nucleotides on both sides of the restriction site of the vector is known. Similarly, the sequence of about 8–20 nucleotides of the ends or of an internal region of the template DNA should preferably be known for the design of the 3' end of the primer.

A general method for preparing oligonucleotides of various lengths and sequences is described by Caracciolo et al.[17] This reference is specifically incorporated herein by reference for this purpose.

In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis, a suitably protected nucleotide having a cyanoethylphosphoramidate at the position to be coupled is reacted with the free hydroxyl of a growing nucleotide chain derivatized to a solid support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate diester linkage. This linkage is stable to acid. Thus, the oxidation to the phosphate or thiophosphate can be conducted at any point during synthesis of the oligonucleotide or after synthesis of the oligonucleotide is complete.

The phosphonates can also be converted to phosphoramidite derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less efficient for oligonucleotides of any substantial length.

Preferred oligonucleotides resistant to in vivo hydrolysis may contain a phosphorothioate substitution at each base[18, 19]. Oligodeoxynucleotides or their phosphorothioate analogues may be synthesized using an Applied Biosystem 380B DNA synthesizer (Applied Biosystems, Inc., Foster City, Calif.).

Using the above approach, the oligonucleotide primer/adapters may be prepared to about 100 nucleotides and to complement sequences of virtually any DNA segment of interest to be amplified or incorporated into a vector.

EXAMPLE 6

Figure 6:
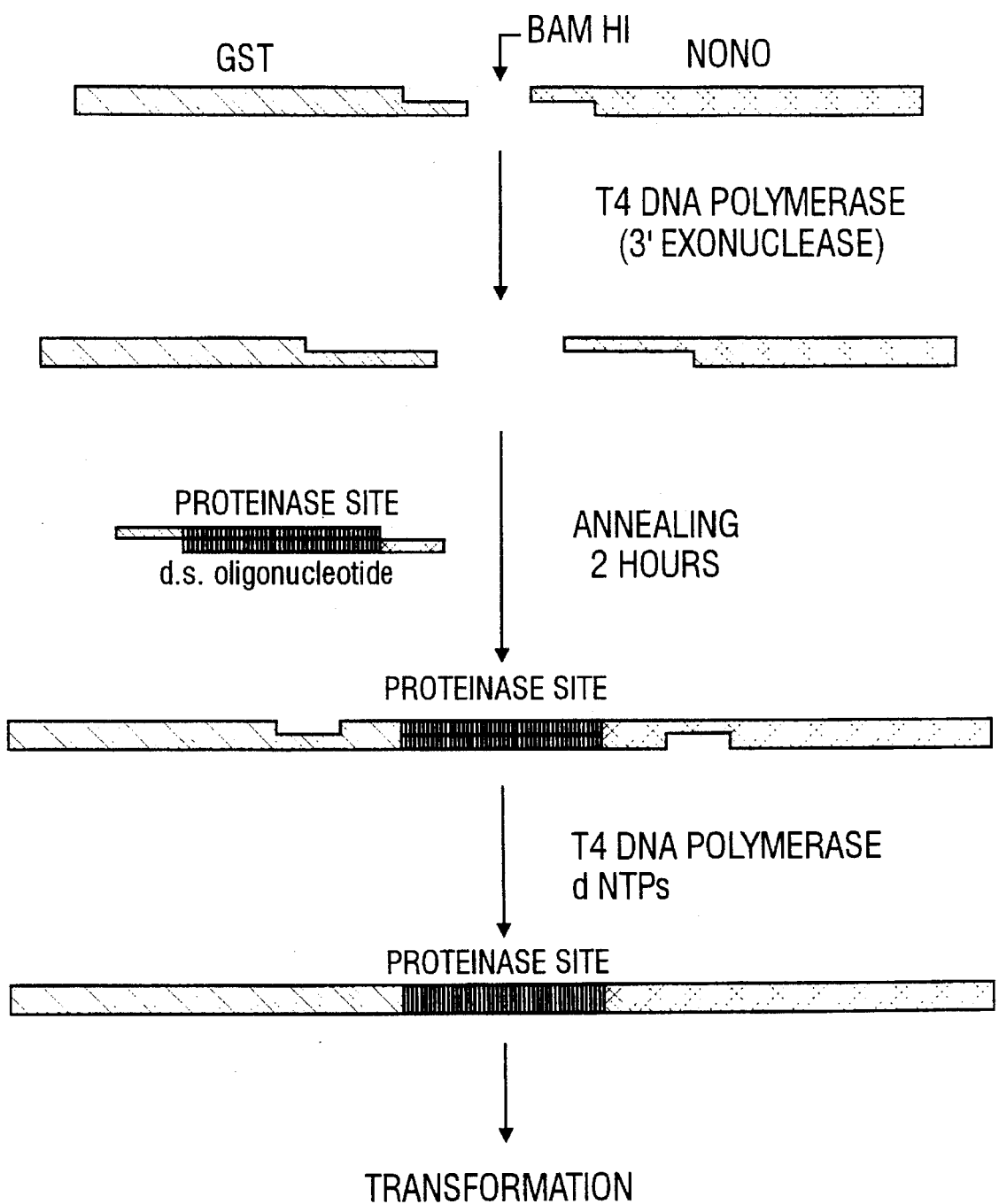
FIG. 6 demonstrates use of the present exonuclease recession method for the incorporation of a proteinase site into a Bam H1 site between the glutathione-S-transferase gene and the nonO gene. The boxes with vertical bars represent the DNA sequence which encodes the TEV proteinase site. The duplexed oligonucleotide containing the proteinase site is labeled. The oligonucleotides are phosphorylated.
Figure 7:
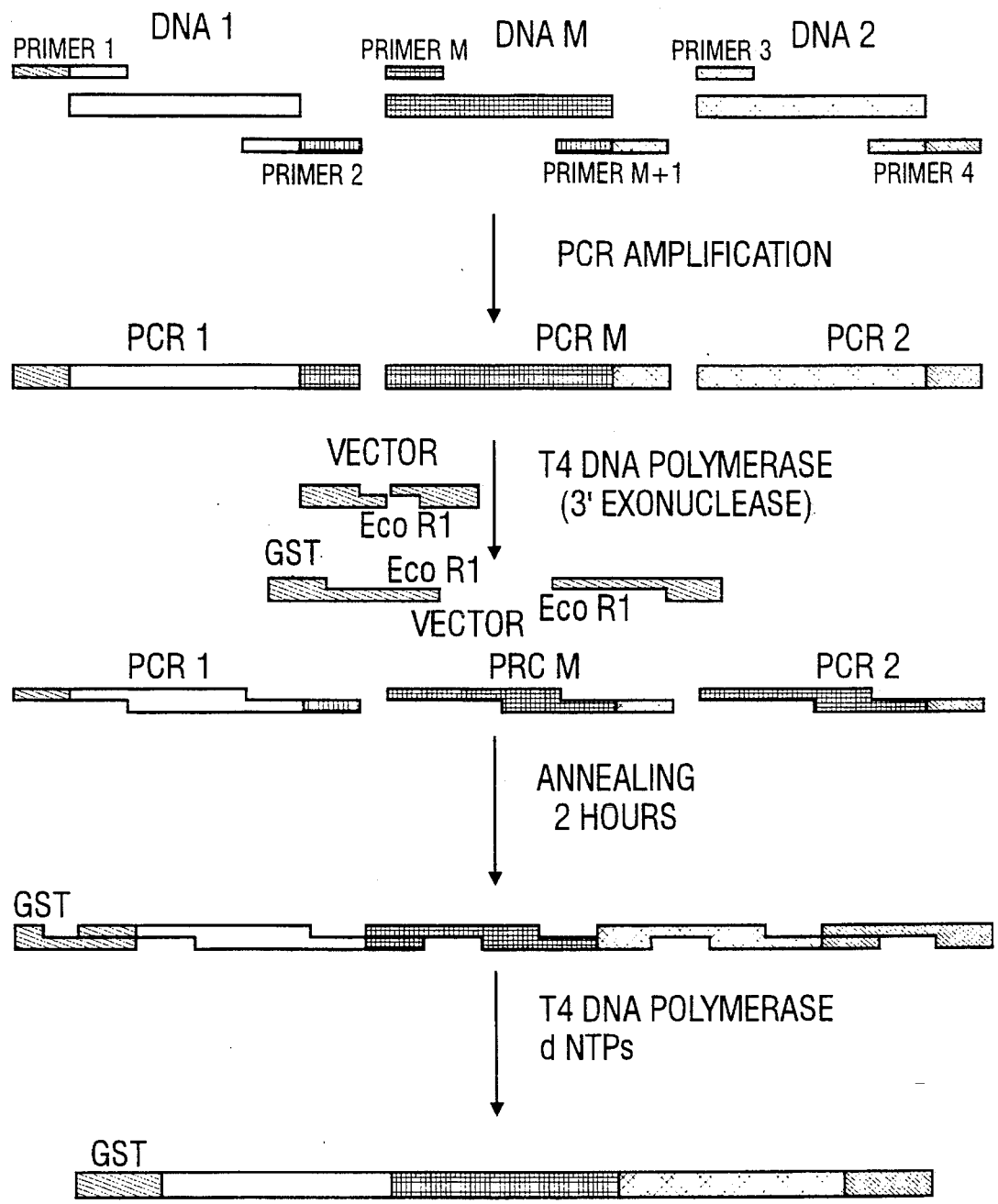
FIG. 7 shows the construction of multiple DNA fragment inserts into a single restriction site in a vector by exonuclease recession. Primers 1, 3 and 4 are designed as in FIG. 4. Primer 2 is designed to have its end sequences overlapping to the end of the middle DNA fragment (DNA M) at its 5' portion. Primers M and M+1 are designed to amplify DNA M. The M+1 primer has its end sequences complementary to the next adjacent molecule, in the case illustrated, it is DNA 2, on its 5' portion. If there is more than one DNA M incorporated, each overlapped 5' portion sequence on primer M+1 will dictate the insert orientation in the molecules. The rest of the symbols and strategies to construct recombinant molecules are essentially the same as in FIG. 1A.

Directional Cloning of an Oligonucleotide Fragment into a Single Restriction Site The present example is provided to demonstrate the exonuclease recession technique for providing directional cloning of an oligonucleotide into a single restriction site. FIG. 6 exemplifies the cloning of a TEV viral proteinase site constructed on a double-stranded oligonucleotide. Vector DNA was linearized at the desired restriction site. For example, the restriction site employed in the present example was the BamH1 restriction site. After cleavage, the DNA was phenol and phenol/chloroform extracted. Following ethanol precipitation, the DNA is resuspended in TE buffer (10 mM Tris, pH 8.0 and 1 mM EDTA) to a final concentration of 0.5 μg/μl.

Figure 8:
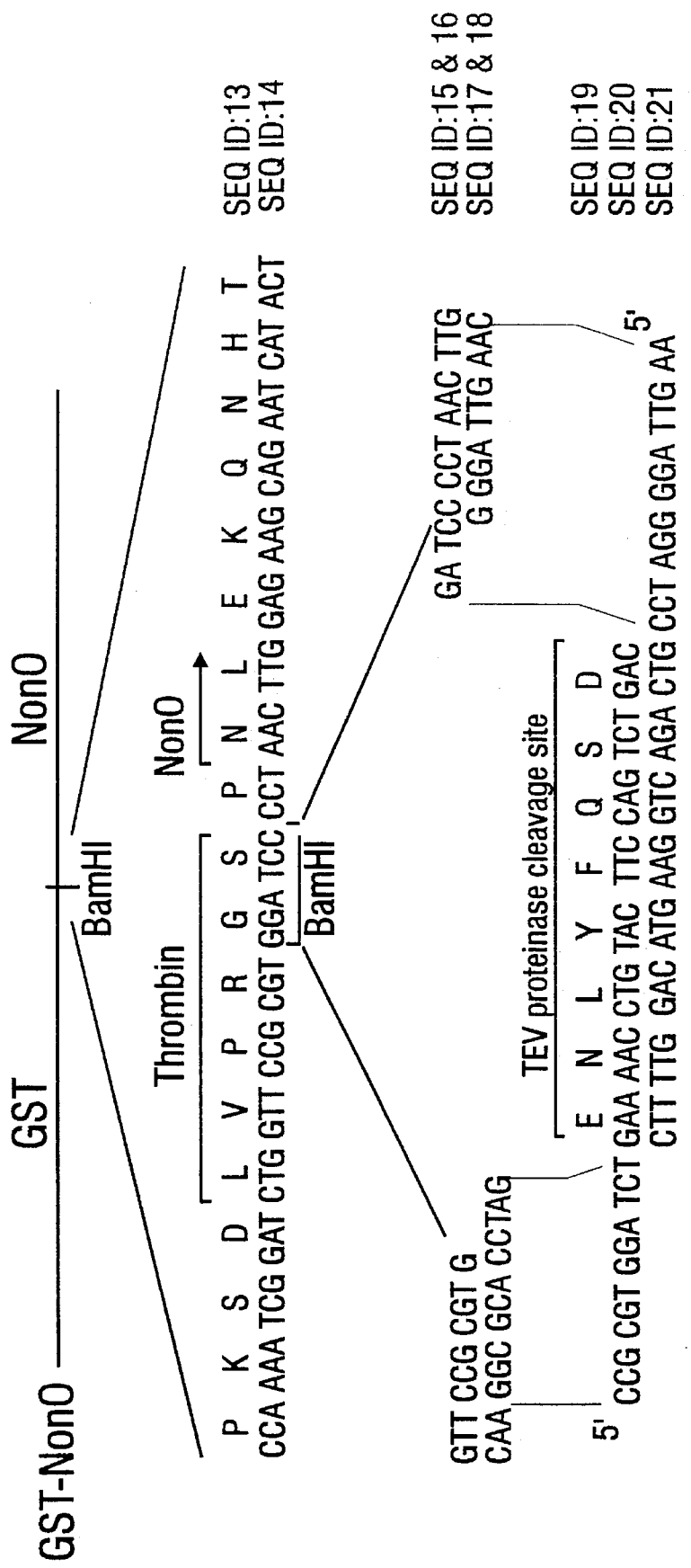
FIG. 8. Insertion of a TEV proteinase cleavage site into an expression construct. Plasmid DNA containing fusion protein construct, GST-nonO, was linearized at Bam HI site between GST and nonO genes. Two synthesized oligonucleotides containing the proteinase cleavage site sequence and the 5' end sequence for annealing to the end of plasmid DNA are in bold face. The regions which overlap with the plasmid end sequences are marked.

A 33-nucleotide long and a 38-nucleotide long oligonucleotide was synthesized. Each oligonucleotide contained two parts, one portion included the desired insertion sequence, and had a sequence that was complementary to the other between two oligonucleotides; the other portion was located at the 5' end of the oligonucleotide, and contained the complementary sequence to one of the end sequences of the vector (see FIG. 6). In the present example, the oligonucleotides used were 5'-CGTGGATCTGAAAACCTG- TACTTCCAGTCTGAC-3' (SEQ ID NO:1) and 5' AAGT- TAGGGGATCCGTCAGACTGGAAGTACAGGTTTTC-3' (SEQ ID NO:2). The strategy to design these oligonucleotides is illustrated in FIG. 8.

The two synthesized oligonucleotides were annealed through their complementary sequences. The duplexed oligonucleotide fragment was purified on a 10% nondenaturing polyacrylamide gel.

Three μg of duplexed oligonucleotide was phosphorylated at the 5' end using T4 polynucleotide kinase. The kinase reaction contained 2.5 μl of 10X kinase buffer (0.5 M Tris-HCl, pH 7.6; 0.1 M $MgCl_2$; 50 mM DTT and 1 mM EDTA), 1 μl of 2 mM ATP, 1.5 units of T4 polynucleotide kinase and $H_2O$ up to a final volume of 25 μl. The reaction mixture was incubated at 37° C. for 30 minutes. After the reaction was complete, the DNA was ethanol precipitated.

Single restriction-enzyme cleaved, linearized vector DNA (0.5 μg) was mixed with 2 μl of 10X T4 DNA polymerase buffer (330 mM Tris-acetate, pH 7.9; 660 mM KOAc; 100 mM $Mg(OAc)_2$; 5 mM DTT and 1 mg/ml BSA), 2 units of T4 DNA polymerase and $H_2O$ up to 20 μl. The enzymatic exonuclease reaction was performed at 37° C. for 2 minutes and immediately stopped by incubation at 70° C. for 10 minutes. The mixture was then slowly cooled to room temperature.

The phosphorylated duplexed oligonucleotide was added into the tube containing the vector DNA mixture. The molar ratio of oligonucleotide insert to vector DNA was calculated at 3 to 1. The mixture was left in the tube at the annealing temperature for at least two hours. Usually the annealing temperature is between 30° C. to 37° C.

One μl of 10X T4 DNA polymerase buffer, 1 μl of 2 mM dNTPs, 1 μl of 10 mM DTT, 4 μl of $H_2O$ and another 2 units of T4 DNA polymerase was added to the mixture which was then incubated at annealing temperature for an additional 30 minutes.

The circularized DNA may be transformed directly into competent bacteria host cells. However, in this oligonucleotide subcloning example, if the circularized DNA is treated with ligase for a short period of time, the transformation efficiency is increased. Three μl of 10X T4 DNA ligase buffer and 1 μl of T4 DNA ligase (20 units) were added to the mixture and incubated for 10 more minutes at the annealing temperature. With this ligase procedure, 206 colonies were obtained with 42 colonies as the vector background compared to 82 colonies from the mixture without ligase treatment. Of those 206 colonies, 12 were randomly picked and 10 of them were found to contain the correctly sized insert. Four of those 10 colonies were further sequenced by femtomole sequencing kit (from Promega), and were found to be in the correct, unique orientation with the correct nucleotide sequence.

In a separate study, 11 colonies were picked for analysis from a plate which did not have ligase treatment before transformation. Four out of the 7 colonies were found to contain the oligonucleotide insert. DNA sequencing through the insert and junction area of these 4 clones revealed that they were all in the correct orientation and contained the expected insert sequence.

EXAMPLE 7

Constructing a Recombinant DNA Molecule with Phosphoducing Gene Insert

Examples 1, 2 and 3 provide the protocol followed for the incorporation of the phosphoducing gene into the vector pGEX-2T. The phosphoducing gene insert was about 700 bp long. The sequence of oligonucleotides used for this example were: 5'-GAGTCTAGAATTACTCGATATCT- TCATCTTCCG (SEQ ID NO:22) and 5'-GGTGGTG GAATTCATAAAATGGAAGAAGCCGCA (SEQ ID NO:23). Clones were identified and expressed to confirm the orientation and sequence.

EXAMPLE 8

Constructing a Recombinant DNA Molecule with Calreticulum Gene Promoter Sequence Insert Examples 1 and 2 provide the protocol followed for the incorporation of the calreticulum gene promoter sequence insert into the vector pGEM-72-CAT. The promoter sequence insert was about 120 bp long.

EXAMPLE 9

Constructing a Recombinant DNA Molecule with Tap1 Gene Insert

Examples 1 and 2 provide the protocol followed for the incorporation of the TAP1 gene into the vector pGEX-KG. The TAP1 gene insert was about 1 kb long.

EXAMPLE 10

Constructing a Recombinant DNA Molecule with Oligomer of Histidine Tag

Example 6 provides the protocol followed for the incorporation of the oligomer of histidine tag insert into the vector pGEX-KG. The histidine tag insert was about 30 and 31 bp long. The oligonucleotides used were 5'-GTCTGACG- GATCCCACCATCATC ACCACCAT-3' (SEQ ID NO:3) and 5'-TCCCGGGGATCAATGGTGGTGATGATGGTG-3' (SEQ ID NO:4).

The following references are incorporated in pertinent part by reference herein for the reasons cited above.

REFERENCES

1. Scharf, S. J. et al. (1986) Science 233, 1076–1078.
2. Vallette, F. et al. (1989) Nucleic Acids Res. 17, 723–732.
3. Hemsley, A. et al. (1989) Nucleic Acids Res. 17, 6545–6551.
4. Clark, J. M. (1988) Nucleic Acids Res. 16, 9677–9686.
5. Jones, D. H. et al. (1990) BioTechniques 8, 178–183.
6. Jones, D. H. et al. (1990) Nature 344, 793–794.

7. Shuldiner, A. R. et al. (1990) Nucleic Acids Res. 18, 1920.

8. Aslanidis, C. and Jong, P. J. (1990) Nucleic Acids Res. 18, 6069–6074.

9. Stoker, A. W. (1990) Nucleic Acids Res. 18, 4290.

10. Kaluz, S. et al. (1992) Nucleic Acids Res. 20, 4369–4370.

11. Buchman, G. W. et al. (1992) Focus 14, 41–45.

12. Yang, Y. S. et al. (1993) Molecular and Cellular Biology 13, 5593–5603.

13. Guan, K. L. and Dixon, J. E. (1991) Annal. Biochem. 192, 262–267.

14. Ho, S. N. et al. (1989) Gene 77, 51–59.

15. Horton, R. M. et al. (1989) Gene 77, 61–68.

16. Innis, M. A. et al. (1988) Proc. Natl. Acad. Sci. USA 85, 9436–9440.

17. Caracciolo et al. (1989) Science 245, 1107.

18. J. Org. Chem. (1990) 55, 4693–4699.

19. Agrawal, S., and Tang, J. Y. (1990) Tetrahedron Letters, 31, 7541.

20. Kuijper et al. (1992) Gene, 112, 147–155.

21. Higuchi, R. "Recombinant PCR," Chapter 22, pgs. 117–183 of PCR Protocols: A Guide to Methods and Applications, 1990, Academic Press, Inc.

22. Lohff and Cease (1991) Nucleic Acids Research, 20 (1), 144.

23. Sambrook et al. (1989) Molecular cloning: A laboratory manual. Cold Spring Harbor, N.Y.

24. Yang et al. (1993) Nucleic Acids Research, 21 (8), 1889–1893.

---

What is claimed is:

1. A method of constructing a recombinant DNA molecule of a first and a second DNA molecule, each molecule having known sequences of at least about 8 nucleotides, the method comprising the steps of:

obtaining a linearized vector DNA molecule, a first and a second linearized DNA molecule, each molecule having a first end and a second end;

obtaining a first primer DNA molecule having a 3' end complementary to the first end of the first DNA molecule and a 5' end complementary to the first end of the linearized vector DNA molecule;

obtaining a second primer DNA molecule having a 3' end complementary to the second end of the first DNA molecule and a 5' end complementary to the first end of the second DNA molecule;

obtaining a third primer DNA molecule complementary to the first end of the second DNA molecule;

obtaining a fourth primer DNA molecule having a 3' end complementary to the second end of the second DNA molecule and a 5' end complementary to the second end of the linearized vector DNA molecule;

annealing the primer molecules to the first and the second DNA molecules to form PCR substrates;

amplifying the PCR substrates to produce PCR products;

treating the PCR products to form recessed PCR products;

treating the linearized vector molecule to form a recessed vector molecule; and annealing the recessed PCR products and the recessed vector molecule;

filling single stranded regions using DNA polymerase; and transforming the filled DNA molecule into a host cell to form said recombinant DNA molecule from said first and second DNA molecule.

2. The method of claim 1 wherein the first and second DNA molecules are separate molecules.

3. The method of claim 1 wherein the first and second DNA molecules are nonoverlapping fragments of one molecule.

4. The method of claim 1 wherein the first or the second DNA molecule has a length from about 12 to about 50,000 nucleotides.

5. The method of claim 1 wherein the first or the second DNA molecule has a length from about 12 to about 10,000 nucleotides.

6. The method of claim 1 wherein the first or the second DNA molecule has a length from about 24 to about 5,000 nucleotides.

7. A method of constructing a recombinant DNA molecule from at least four DNA molecules, each molecule having known end sequences of at least about 8 nucleotides, the method comprising the steps of:

obtaining a linearized vector DNA molecule, a first and a second linearized DNA molecule, each molecule having a first end and a second end;

obtaining at least one internal DNA molecule having a first end and a second end;

obtaining a first primer DNA molecule having a 3' end complementary to the first end of the first DNA molecule and a 5' end complementary to the first end of the linearized vector DNA molecule;

obtaining a second primer DNA molecule having a 3' end complementary to the second end of the first DNA molecule and a 5' end complementary to the first end of said at least one internal DNA molecule;

obtaining a primer DNA molecule complementary to the first end of said at least one internal DNA molecule;

obtaining a primer DNA molecule having a 3' end complementary to the second end of said at least one internal DNA molecule and a 5' end complementary to the first end of one other internal DNA molecule;

obtaining a primer DNA molecule having a 3' end complementary to the second end of said other internal DNA molecule and a 5' end complementary to the first end of the second DNA molecule;

obtaining a third primer DNA molecule complementary to the first end of the second DNA molecule;

obtaining a fourth primer DNA molecule having a 3' end complementary to the second end of the second DNA molecule and a 5' end complementary to the second end of the vector DNA molecule;

annealing the primer molecules to the first, the second and the internal DNA molecules to form PCR substrates;

amplifying the PCR substrates to produce PCR products;

treating the PCR products to form recessed PCR products;

treating the linearized vector molecule to form a recessed vector molecule; and annealing the recessed PCR products and the recessed vector molecule;

filling single stranded regions using DNA polymerase; and transforming the DNA molecule into a host cell to form said recombinant DNA molecule from said at least four DNA fragments.

8. The method of claim 7 wherein the first, the second or the internal DNA molecule has a length from about 12 to about 50,000 nucleotides.

9. The method of claim 7 wherein the first, the second or the internal DNA molecule has a length from about 12 to about 10,000 nucleotides.

10. The method of claim 7 wherein the first, the second or the internal DNA molecule has a length from about 24 to about 5,000 nucleotides.

11. The method of claim 7 wherein the recombinant molecule is constructed from four DNA molecules.

12. A method of constructing a site-directed mutation in a recombinant DNA molecule comprising:

obtaining a template DNA molecule having a first end, an internal region for mutation and a second end, each end having a known sequence of at least about 8 nucleotides and the internal region for mutation having a known sequence of at least about 16 nucleotides;

obtaining a linearized vector DNA molecule having a first end and a second end, each end having a known sequence of at least about 8 nucleotides;

obtaining a first primer DNA molecule having a 3' end complementary to at least about 8 nucleotides of the known sequence of the first end of the template DNA molecule and a 5' end complemetary to at least about 8 nucleotides of the known sequence of the first end of the vector DNA molecule;

obtaining a second primer DNA molecule having a 3' end complementary to at least about 8 nucleotides of a region 5' to the internal region for mutation of the template DNA molecule, a mutation region, and a 5' end complementary to at least about 8 nucleotides of a region 3' to the internal region for mutation of the template DNA molecule;

obtaining a third primer DNA molecule having a 3' end complementary to at least about 8 nucleotides of a region 3' to the internal region for mutation of the template DNA molecule, a mutation region complementary to the mutation region of the second primer DNA molecule and a 5' end complementary to at least about 8 nucleotides of a region 5' to the internal region for mutation of the template DNA molecule;

obtaining a fourth primer DNA molecule having a 3' end complementary to at least about 8 nucleotides of the known sequence of the second end of the template DNA molecule and a 5' end complementary to at least about 8 nucleotides of the known sequence of the second end of the vector DNA molecule;

annealing the primer molecules to the template molecule to form a PCR substrate;

amplifying the PCR substrate to produce PCR products;

treating the PCR products to form recessed PCR products;

treating the linearized vector molecule to form a recessed vector molecule; and annealing the recessed PCR products and the recessed vector molecule;

filling Single stranded regions using DNA polymerase; and transforming the filled DNA molecule into a host cell to form said site-directed mutation in said recombinant DNA molecule.

13. The method of claim 12 wherein the mutation region of the second primer contains an insertion, deletion or substitution of at least one nucleotide.

14. The method of claim 12 wherein the template DNA molecule has a length from about 12 to about 50,000 nucleotides.

15. The method of claim 12 wherein the template DNA molecule has a length from about 12 to about 10,000 nucleotides.

16. The method of claim 12 wherein the template DNA molecule has a length from about 24 to about 5,000 nucleotides.

17. A method of constructing a recombinant DNA molecule containing an oligonucleotide fragment comprising:

obtaining a linearized vector DNA molecule having a first end and a second end, each end having a known sequence of at least about 8 nucleotides;

treating the linearized vector DNA molecule to form a recessed vector DNA molecule;

preparing a double stranded oligonucleotide having single stranded ends of at least 8 nucleotides of known sequence;

reacting the double stranded oligonucleotide in a kinase reaction to form a phosphorylated double stranded oligonucleotide; and annealing the phosphorylated double stranded oligonucleotide and the recessed vector DNA molecule;

filling single stranded regions using DNA polymerase; and transforming the DNA molecule into a host cell to form said recombinant DNA molecule containing said oligoncleotide fragment.

18. The method of claim 17 wherein the double stranded oligonucleotide is from about 20 to about 100 nucleotides in length.

19. The method of claim 17 wherein the double stranded oligonucleotide is from about 30 to about 50 nucleotides in length.

20. A method of constructing a recombinant DNA molecule comprising a nonO gene comprising:

obtaining at least a first and a second linearized DNA molecules:

obtaining at least two bipartite oligonucleotide primer molecules, each having a first portion which primes a PCR extension of the first linearized DNA molecule containing the nonO gene and a second portion which is complementary to the second linearized DNA molecule:

annealing the primer molecules to the first linearized DNA molecule to form a PCR substrate:

amplifying the PCR substrate to produce a PCR product:

treating the PCR product to form a recessed PCR product:

treating the second linearized DNA molecule to form a recessed DNA molecule:

annealing the recessed PCR product to the recessed DNA molecule filling single stranded regions using DNA polymerase; and transforming the filled DNA molecule into a host cell to form said recombinant DNA molecule.

21. The method of claim 20 wherein more than two linearized DNA molecules are obtained and an additional set of bipartite primers is obtained for each additional linearized DNA molecule.

22. The method of claim 20 wherein the first DNA molecule is a template DNA molecule and the second DNA molecule is a vector DNA molecule.

23. The method of claim 22 wherein the template DNA molecule containing a nonO gene has at least two known sequences of about 12 nucleotides.

24. The method of claim 22 wherein the template DNA molecule comprises two molecules of DNA, each molecule having a first end and a second end with known sequences of between about 8–20 nucleotides.

25. The method of claim 22 wherein the template DNA molecule comprises a region to be deleted and further known sequences are flanking the region to be deleted.

26. The method of claim 22 wherein the template DNA molecule comprises a sense and an antisense strand, the first primer DNA molecule is complementary to a portion of the sense strand and the second primer DNA molecule is complementary to a portion of the antisense strand.

27. A method of constructing a recombinant DNA molecule containing a nonO gene comprising:

obtaining a linearized vector DNA molecule and a template DNA molecule containing the nonO gene, each molecule having a first end and a second end, each end having a known sequence of at least about 8 nucleotides;

obtaining a first primer DNA molecule having a 3' end complementary to the first end of the template DNA molecule and a second primer DNA molecule having a 3' end complementary to the second end of the template DNA molecule, the first and second primers having 5' ends complementary to the known sequence of the first and second ends of the vector DNA, respectively;

annealing the primer DNA molecules to the template DNA molecule to form a PCR substrate, amplifying the PCR substrate to produce a PCR product;

treating the PCR product to form a recessed PCR product;

treating the linearized vector DNA molecule to form a recessed vector DNA molecule: and annealing the recessed PCR product and the recessed vector DNA molecule:

filling single stranded regions using DNA polymerase; and transforming the filled DNA molecule into a host cell to form said recombinant DNA molecule.

28. The method of claim 27 wherein the template DNA molecule containing said nonO gene has at least two known sequences of about 12 nucleotides.

29. The method of claim 27 wherein the template DNA molecule containing said nonO gene comprises two molecules of DNA, each molecule having a first end and a second end with known sequences of between about 8–20 nucleotides.

30. The method of claim 27 wherein the template DNA molecule containing said nonO gene comprises a region to be deleted and further known sequences are flanking the region to be deleted.

31. The method of claim 27 wherein the template DNA molecule containing said nonO gene comprises a sense anti an antisense strand, the first primer DNA molecule is complementary to a portion of the sense strand and the second primer DNA molecule is complementary to a portion of the antisense strand.

32. The method of claim 20 or 27 further comprising a step of adding a nucleotide residue to or of said primer DNA molecules to form an extended primer DNA molecule before the first annealing step.

33. The method of claim 20 or 27 wherein the PCR product is treated with a strand-specific exonuclease to produce the recessed PCR product.

34. The method of claim 22 or 27 wherein the template DNA molecule has at least two known sequences of between about 8 to about 20 nucleotides.

35. The method of claim 22 or 27 wherein the template DNA molecule is an oligonucleotide.

36. The method of claim 22 or 27 wherein the template DNA molecule comprises a sense and an antisense strand, the first primer DNA molecule is complementary to a portion of the antisense strand and the second primer DNA molecule is complementary to a portion of the sense strand.

37. The method of claim 22 or 27 wherein the template DNA molecule has a length from about 12 to about 50,000 nucleotides.

38. The method of claim 22 or 27 wherein the template DNA molecule has a length from about 12 to about 10,000 nucleotides.

39. The method of claim 22 or 27 wherein the template DNA molecule has a length from about 24 to about 5,000 nucleotides.

40. The method of claim 22 or 27 wherein the vector DNA molecule is pGEX-KG and the method includes the step of adding a dAMP residue to the second primer DNA molecule to form an extended second primer DNA molecule before the first annealing step.

41. The method of claim 20, 27, 1, 7 or 12 wherein the PCR substrate is amplified with Taq DNA polymerase.

42. The method of claim 20, 27, 1, 7 or 12 wherein the PCR substrate is amplified with Vent DNA polymerase or PFU DNA polymerase.

43. The method of claim 1, 7, 12, 17, 20 or 27 wherein the vector DNA molecule is a prokaryotic vector DNA molecule.

44. The method of claim 1, 7, 12, 17, 20 or 27 wherein the vector DNA molecule is a eukaryotic vector DNA molecule.

45. The method of claim 1, 7, 12, 17, 20 or 27 wherein the vector DNA molecule is an expression vector DNA molecule.

46. The method of claim 1, 7, 12, 17, 20 or 27 wherein the vector DNA molecule is a cloning vector DNA molecule.

47. The method of claim 1, 7, 12, 17, 20 or 27 wherein the vector DNA molecule ms pGEX-KG.

48. The method of claim 1, 7, 12, 17, 20 or 27 wherein the vector DNA molecule ms pGEM-7Z-CAT.

49. The method of claim 1, 7, 12, 17, 20 or 27 wherein the linearized vector DNA molecule is pGEX-KG linearized with EcoRI.

50. The method of claim 1, 7, 12, 17, 20 or 27 wherein the linearized vector DNA molecule is pGEM-7Z-CAT linearized with BamHI.

51. The method of claim 1, 7, 12, 17, 20 or 27 wherein the vector DNA molecule was linearized by a single restriction enzyme cleavage.

52. The method of claim 1, 7, 12, 17, 20 or 27 wherein the vector DNA molecule was linearized by a double restriction enzyme cleavage.

53. The method of claim 1, 7, 12, 17, 20 or 27 wherein the linearized vector DNA molecule has a known sequence of about 12 nucleotides on at least one end.

54. The method of claim 1, 7, 12, 17, 20 or 27 wherein the linearized vector DNA molecule is treated with a strand-specific exonuclease to produce the recessed vector DNA molecule.

55. The method of claim 54 wherein the exonuclease is the 3' exonuclease of T4 DNA polymerase.

56. The method of claim 54 wherein the exonuclease is Exonuclease III.

* * * * *

UNITED STATES PATENT AND TRADEMARK OFFICE
CERTIFICATE OF CORRECTION

PATENT NO. : 5,580,759
DATED : December 3, 1996
INVENTOR(S) : Yang et al.

It is certified that error appears in the above-identified patent and that said Letters Patent is hereby corrected as shown below:

In column 11, line 19, please replace "glutathione-S transferase" with --glutathione-S-transferase--.

In column 11, lines 33-34, please replace "p. 13, line 25 to p. 14, line 24" with --column 7, lines 5-43--.

In column 14, lines 37-38, please replace "glutathione-S transferase" with --glutathione-S-transferase--.

In column 17, line 16, please replace "5' AAGT-" with --5'-AAGT---.

In column 17, line 26, please replace "μ1" with --μl--.

In column 18, line 51, please replace "GATCCCACCATCATC ACCACCAT-3'" with --GATCCCACCATCATCACCACCAT-3'--.

In column 19, line 10, please replace "Y. S." with --Y.-S.--.

In claim 1, column 28, line 64, please delete "and".

In claim 1, column 29, line 2, please begin a new paragraph before "and".

In claim 1, column 29, line 3, please replace "from" with --of--.

In claim 1, column 29, line 4, please insert --said-- between "and" and "second".

In claim 7, column 29, line 59, please delete "and".

In claim 7, column 29, line 65, please insert --filled-- between "the" and "DNA".

UNITED STATES PATENT AND TRADEMARK OFFICE
CERTIFICATE OF CORRECTION

PATENT NO. : 5,580,759

DATED : December 3, 1996

INVENTOR(S) : Yang et al.

It is certified that error appears in the above-identified patent and that said Letters Patent is hereby corrected as shown below:

In claim 12, column 30, line 53, please delete "and".
In claim 12, column 30, line 56, please replace "Single" with --single--.
In claim 17, column 31, line 19, please delete "and"
In claim 17, column 31, line 25, please insert --filled-- between "the" and "DNA".
In claim 20, column 31, line 52, please insert --;-- after "molecule".
In claim 27, column 32, line 32, please replace ": and" with --;--.
In claim 27, column 32, line 34, please replace ":" with --;--.
In claim 28, column 32, line 41, please replace "said" with --the--.
In claim 29, column 32, line 44, please replace "said" with --the--.
In claim 30, column 32, line 49, please replace "said" with --the--.
In claim 31, column 32, line 53, please replace "said" with --the--, and please replace "anti" with --and--.
In claim 32, column 32, line 59, please replace "or" with --one--.
In claim 40, column 33, line 18, please replace the first "the" with --a--.
In claim 43, column 33, line 27, please replace "20" with --22--.
In claim 44, column 33, line 30, please replace "20" with --22--.
In claim 45, column 33, line 32, please replace "20" with --22--.

UNITED STATES PATENT AND TRADEMARK OFFICE
CERTIFICATE OF CORRECTION

PATENT NO.   : 5,580,759
DATED        : December 3, 1996
INVENTOR(S)  : Yang et al.

It is certified that error appears in the above-identified patent and that said Letters Patent is hereby corrected as shown below:

In claim 46, column 34, line 1, please replace "20" with --22--.
In claim 47, column 34, line 3, please replace "20" with --22--.
In claim 47, column 34, line 4, please replace "ms" with --is--.
In claim 48, column 34, line 6, please replace "20" with --22--.
In claim 48, column 34, line 7, please replace "ms" with --is--.
In claim 49, column 34, line 8, please replace "20" with --22--.
In claim 50, column 34, line 11, please replace "20" with --22--.
In claim 51, column 34, line 14, please replace "20" with --22--.
In claim 52, column 34, line 18, please replace "20" with --22--.
In claim 53, column 34, line 21, please replace "20" with --22--.
In claim 54, column 34, line 24, please replace "20" with --22--.

Signed and Sealed this

Fourteenth Day of April, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 33 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:1:

CGTGGATCTG AAAACCTGTA CTTCCAGTCT GAC        33

( 2 ) INFORMATION FOR SEQ ID NO:2:

( i ) SEQUENCE CHARACTERISTICS:
        ( A ) LENGTH: 38 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:2:

AAGTTAGGGG ATCCGTCAGA CTGGAAGTAC AGGTTTTC        38

( 2 ) INFORMATION FOR SEQ ID NO:3:

( i ) SEQUENCE CHARACTERISTICS:
        ( A ) LENGTH: 31 base pairs
        ( B ) TYPE: Nucleic acid
        ( C ) STRANDEDNESS: single
        ( D ) TOPOLOGY: Linear ( i i ) MOLECULE TYPE: Oligonucleotide ( x i ) SEQUENCE DESCRIPTION: SEQ ID NO:3:

GTCTGACGGA TCCCACCATC ATCACCACCA T        31

( 2 ) INFORMATION FOR SEQ ID NO:4:

( i ) SEQUENCE CHARACTERISTICS:
        ( A ) LENGTH: 30 base pairs (B) TYPE: Nucleic acid
(C) STRANDEDNESS: single
(D) TOPOLOGY: Linear (ii) MOLECULE TYPE: Oligonucleotide (xi) SEQUENCE DESCRIPTION: SEQ ID NO:4:

TCCCGGGGAT CAATGGTGGT GATGATGGTG　　　　　　　　　　30

(2) INFORMATION FOR SEQ ID NO:5:

(i) SEQUENCE CHARACTERISTICS:
　　(A) LENGTH: 12 base pairs
　　(B) TYPE: Nucleic acid
　　(C) STRANDEDNESS: Single
　　(D) TOPOLOGY: Linear (ii) MOLECULE TYPE: Oligonucleotide (xi) SEQUENCE DESCRIPTION: SEQ ID NO:5:

GGTGGTGGAA TT　　　　　　　　　　12

(2) INFORMATION FOR SEQ ID NO:6:

(i) SEQUENCE CHARACTERISTICS:
　　(A) LENGTH: 17 base pairs
　　(B) TYPE: Nucleic acid
　　(C) STRANDEDNESS: Single
　　(D) TOPOLOGY: Linear (ii) MOLECULE TYPE: Oligonucleotide (xi) SEQUENCE DESCRIPTION: SEQ ID NO:6:

TCCGGTGGTG GTGGTGG　　　　　　　　　　17

(2) INFORMATION FOR SEQ ID NO:7:

(i) SEQUENCE CHARACTERISTICS:
　　(A) LENGTH: 22 base pairs
　　(B) TYPE: Nucleic acid
　　(C) STRANDEDNESS: single
　　(D) TOPOLOGY: Linear (ii) MOLECULE TYPE: Oligonucleotide (xi) SEQUENCE DESCRIPTION: SEQ ID NO:7:

AATTCTAGAC TCCATGGGTC GA　　　　　　　　　　22

(2) INFORMATION FOR SEQ ID NO:8:

(i) SEQUENCE CHARACTERISTICS:
　　(A) LENGTH: 21 base pairs
　　(B) TYPE: Nucleic acid
　　(C) STRANDEDNESS: single
　　(D) TOPOLOGY: Linear (ii) MOLECULE TYPE: Oligonucleotide (xi) SEQUENCE DESCRIPTION: SEQ ID NO:8:

AATTCCACCA CCACCACGG A　　　　　　　　　　21

(2) INFORMATION FOR SEQ ID NO:9:

(i) SEQUENCE CHARACTERISTICS:
　　(A) LENGTH: 18 base pairs
　　(B) TYPE: Nucleic acid
　　(C) STRANDEDNESS: single
　　(D) TOPOLOGY: Linear (ii) MOLECULE TYPE: Oligonucleotide ( x i ) SEQUENCE DESCRIPTION: SEQ ID NO:9:

TCGACCCATG GAGTCTAG    18

( 2 ) INFORMATION FOR SEQ ID NO:10:

( i ) SEQUENCE CHARACTERISTICS:
        ( A ) LENGTH: 7 amino acid residues
        ( B ) TYPE: Amino acid
        ( C ) STRANDEDNESS: single
        ( D ) TOPOLOGY: Linear ( i i ) MOLECULE TYPE: Protein ( x i ) SEQUENCE DESCRIPTION: SEQ ID NO:10:

Ser Gly Gly Gly Gly Gly Ile
1               5

( 2 ) INFORMATION FOR SEQ ID NO:11:

( i ) SEQUENCE CHARACTERISTICS:
        ( A ) LENGTH: 6 amino acid residues
        ( B ) TYPE: Amino acid
        ( C ) STRANDEDNESS: single
        ( D ) TOPOLOGY: Linear ( i i ) MOLECULE TYPE: Protein ( x i ) SEQUENCE DESCRIPTION: SEQ ID NO:11:

Leu Asp Ser Met Gly Arg
1               5

( 2 ) INFORMATION FOR SEQ ID NO:12:

( i ) SEQUENCE CHARACTERISTICS:
        ( A ) LENGTH: 13 base pairs
        ( B ) TYPE: Nucleic acid
        ( C ) STRANDEDNESS: single
        ( D ) TOPOLOGY: Linear ( i i ) MOLECULE TYPE: Oligonucleotide ( x i ) SEQUENCE DESCRIPTION: SEQ ID NO:12:

GAGTCTAGAA TTA    13

( 2 ) INFORMATION FOR SEQ ID NO:13:

( i ) SEQUENCE CHARACTERISTICS:
        ( A ) LENGTH: 19 amino acid residues
        ( B ) TYPE: Amino acid
        ( C ) STRANDEDNESS: single
        ( D ) TOPOLOGY: Linear ( i i ) MOLECULE TYPE: Protein ( x i ) SEQUENCE DESCRIPTION: SEQ ID NO:13:

Pro Lys Ser Asp Leu Val Pro Arg Gly Ser Pro Asn Leu Glu Lys Gln
1               5                   10                  15
Asn His Thr ( 2 ) INFORMATION FOR SEQ ID NO:14:

( i ) SEQUENCE CHARACTERISTICS:
        ( A ) LENGTH: 57 base pairs
        ( B ) TYPE: Nucleic acid
        ( C ) STRANDEDNESS: single
        ( D ) TOPOLOGY: Linear ( i i ) MOLECULE TYPE: Oligonucleotide (x i) SEQUENCE DESCRIPTION: SEQ ID NO:14:

CCAAAATCGG ATCTGGTTCC GCGTGGATCC CCTAACTTGG AGAAGCAGAA TCATACT      57

(2) INFORMATION FOR SEQ ID NO:15:

(i) SEQUENCE CHARACTERISTICS:
        (A) LENGTH: 10 base pairs
        (B) TYPE: Nucleic acid
        (C) STRANDEDNESS: single
        (D) TOPOLOGY: Linear (i i) MOLECULE TYPE: Oligonucleotide (x i) SEQUENCE DESCRIPTION: SEQ ID NO:15:

GTTCCGCGTG      10

(2) INFORMATION FOR SEQ ID NO:16:

(i) SEQUENCE CHARACTERISTICS:
        (A) LENGTH: 14 base pairs
        (B) TYPE: Nucleic acid
        (C) STRANDEDNESS: single
        (D) TOPOLOGY: Linear (i i) MOLECULE TYPE: Oligonucleotide (x i) SEQUENCE DESCRIPTION: SEQ ID NO:16:

GATCCCCTAA CTTG      14

(2) INFORMATION FOR SEQ ID NO:17:

(i) SEQUENCE CHARACTERISTICS:
        (A) LENGTH: 14 base pairs
        (B) TYPE: Nucleic acid
        (C) STRANDEDNESS: single
        (D) TOPOLOGY: Linear (i i) MOLECULE TYPE: Oligonucleotide (x i) SEQUENCE DESCRIPTION: SEQ ID NO:17:

GATCCACGCG GAAC      14

(2) INFORMATION FOR SEQ ID NO:18:

(i) SEQUENCE CHARACTERISTICS:
        (A) LENGTH: 10 base pairs
        (B) TYPE: Nucleic acid
        (C) STRANDEDNESS: single
        (D) TOPOLOGY: Linear (i i) MOLECULE TYPE: Oligonucleotide (x i) SEQUENCE DESCRIPTION: SEQ ID NO:18:

CAAGTTAGGG      10

(2) INFORMATION FOR SEQ ID NO:19:

(i) SEQUENCE CHARACTERISTICS:
        (A) LENGTH: 8 amino acid residues
        (B) TYPE: Amino acid
        (C) STRANDEDNESS: single
        (D) TOPOLOGY: Linear (i i) MOLECULE TYPE: Protein (x i) SEQUENCE DESCRIPTION: SEQ ID NO:19:

Glu Asn Leu Tyr Phe Gln Ser Asp
1               5

( 2 ) INFORMATION FOR SEQ ID NO:20:

( i ) SEQUENCE CHARACTERISTICS:
        ( A ) LENGTH: 36 base pairs
        ( B ) TYPE: Nucleic acid
        ( C ) STRANDEDNESS: single
        ( D ) TOPOLOGY: Linear ( i i ) MOLECULE TYPE: Oligonucleotide ( x i ) SEQUENCE DESCRIPTION: SEQ ID NO:20:

CCGCGTGGAT CTGAAAACCT GTACTTCCAG TCTGAC      36

( 2 ) INFORMATION FOR SEQ ID NO:21:

( i ) SEQUENCE CHARACTERISTICS:
        ( A ) LENGTH: 38 base pairs
        ( B ) TYPE: Nucleic acid
        ( C ) STRANDEDNESS: single
        ( D ) TOPOLOGY: Linear ( i i ) MOLECULE TYPE: Oligonucleotide ( x i ) SEQUENCE DESCRIPTION: SEQ ID NO:21:

AAGTTAGGGG ATCCGTCAGA CTGGAAGTAC AGGTTTTC      38

( 2 ) INFORMATION FOR SEQ ID NO:22:

( i ) SEQUENCE CHARACTERISTICS:
        ( A ) LENGTH: 33 base pairs
        ( B ) TYPE: Nucleic acid
        ( C ) STRANDEDNESS: single
        ( D ) TOPOLOGY: Linear ( i i ) MOLECULE TYPE: Oligonucleotide ( x i ) SEQUENCE DESCRIPTION: SEQ ID NO:22:

GAGTCTAGAA TTACTCGATA TCTTCATCTT CCG      33

( 2 ) INFORMATION FOR SEQ ID NO:23:

( i ) SEQUENCE CHARACTERISTICS:
        ( A ) LENGTH: 33 base pairs
        ( B ) TYPE: Nucleic acid
        ( C ) STRANDEDNESS: single
        ( D ) TOPOLOGY: Linear ( i i ) MOLECULE TYPE: Oligonucleotide ( x i ) SEQUENCE DESCRIPTION: SEQ ID NO:23:

GGTGGTGGAA TTCATAAAAT GGAAGAAGCC GCA      33